United States Patent
Nishihara et al.

(10) Patent No.: US 7,939,627 B2
(45) Date of Patent: May 10, 2011

(54) PEPTIDES COMPRISING AN EPITOPE OF THE WILMS TUMOR GENE PRODUCT

(75) Inventors: Toshio Nishihara, Osaka (JP); Masashi Gotoh, Osaak (JP)

(73) Assignees: International Institute of Cancer Immunology, Suita-shi (JP); Chugai Seiyaku Kabushiki Kaisha, Tokyo (JP); Dainippon Sumitomo Pharma Co., Ltd., Osaka-shi (JP)

( * ) Notice: Subject to any disclaimer, the term of this patent is extended or adjusted under 35 U.S.C. 154(b) by 311 days.

(21) Appl. No.: 12/095,418

(22) PCT Filed: Nov. 29, 2006

(86) PCT No.: PCT/JP2006/323827
§ 371 (c)(1),
(2), (4) Date: May 29, 2008

(87) PCT Pub. No.: WO2007/063903
PCT Pub. Date: Jun. 7, 2007

(65) Prior Publication Data
US 2010/0062010 A1    Mar. 11, 2010

(30) Foreign Application Priority Data
Nov. 30, 2005   (JP) .................. 2005-346577

(51) Int. Cl.
*A61K 38/08*    (2006.01)
(52) U.S. Cl. .............. 530/328; 530/327; 424/184.1; 424/185.1; 514/21.6
(58) Field of Classification Search .......... 530/328, 530/327; 424/184.1, 185.1
See application file for complete search history.

(56) References Cited

U.S. PATENT DOCUMENTS

| | | | |
|---|---|---|---|
| 7,030,212 B1* | 4/2006 | Sugiyama et al. | 530/328 |
| 7,326,767 B1 | 2/2008 | Stauss et al. | |
| 7,342,092 B2* | 3/2008 | Sugiyama | 530/324 |
| 7,378,384 B2* | 5/2008 | Sugiyama et al. | 514/2 |
| 7,390,871 B2* | 6/2008 | Sugiyama et al. | 530/300 |
| 7,420,034 B2* | 9/2008 | Sugiyama et al. | 530/328 |
| 7,517,950 B2* | 4/2009 | Sugiyama et al. | 530/300 |
| 7,608,685 B1* | 10/2009 | Sugiyama et al. | 530/300 |
| 7,666,985 B2* | 2/2010 | Sugiyama et al. | 530/328 |
| 2004/0097703 A1* | 5/2004 | Sugiyama | 530/324 |
| 2004/0247609 A1* | 12/2004 | Sugiyama | 424/185.1 |
| 2005/0002951 A1* | 1/2005 | Sugiyama et al. | 424/185.1 |
| 2006/0093615 A1 | 5/2006 | Sugiyama et al. | |
| 2006/0205667 A1 | 9/2006 | Sugiyama et al. | |
| 2006/0217297 A1* | 9/2006 | Sugiyama et al. | 514/12 |
| 2007/0128207 A1* | 6/2007 | Sugiyama | 424/185.1 |
| 2008/0070835 A1 | 3/2008 | Sugiyama | |
| 2008/0152631 A1 | 6/2008 | Sugiyama | |
| 2008/0159993 A1 | 7/2008 | Stauss et al. | |
| 2009/0143291 A1* | 6/2009 | Sugiyama et al. | 514/12 |
| 2009/0263409 A1* | 10/2009 | Sugiyama | 424/185.1 |
| 2010/0062010 A1* | 3/2010 | Nishihara et al. | 424/184.1 |

FOREIGN PATENT DOCUMENTS

| | | |
|---|---|---|
| EP | 1 548 028 A1 | 6/2005 |
| EP | 1 584 627 A1 | 10/2005 |
| WO | WO 00/18795 | 4/2000 |

OTHER PUBLICATIONS

U.S. Appl. No. 12/554,151, filed Sep. 4, 2009, Sugiyama.
U.S. Appl. No. 12/280,268, filed Aug. 21, 2008, Sugiyama.
U.S. Appl. No. 12/521,533, filed Jun. 26, 2009, Sugiyama.
U.S. Appl. No. 12/449,765, filed Aug. 26, 2009, Sugiyama.
U.S. Appl. No. 12/529,701, filed Sep. 2, 2009, Sugiyama.
U.S. Appl. No. 12/366,200, filed Feb. 5, 2009, Sugiyama, et al.
U.S. Appl. No. 12/552,660, filed Sep. 2, 2009, Sugiyama.
David Cosman, et al., "A Novel Immunoglobulin Superfamily Receptor for Cellular and Viral MHC Class I Molecules", Immunity, vol. 7, Aug. 1997, pp. 273-282.
David J. Kittlesen, "Human Melanoma Patients Recognize an HLA-A1-Restricted CTL Epitope from Tyrosinase Containing Two Cysteine Residues: Implications for Tumor Vaccine Development[1]", The American Association of Immunologists, vol. 160, 1998, pp. 2099-2106.
Katherine M. Call, "Isolation and Characterization of a Zinc Finger Polypeptide Gene at the Human Chromosome 11 Wilms' Tumor Locus", Cell, vol. 60, Feb. 9, 1990, pp. 509-520.

(Continued)

*Primary Examiner* — David Lukton
(74) *Attorney, Agent, or Firm* — Oblon, Spivak, McClelland, Maier & Neustadt, L.L.P.

(57) ABSTRACT

A compound of formula (1):

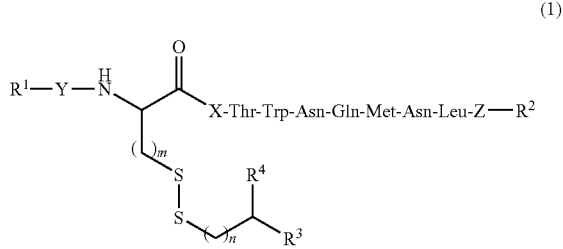

(1)

wherein X is a tyrosine residue or a methionine residue; Y and Z each are a single bond; $R^1$ is a hydrogen atom; $R^2$ is a hydroxy group; $R^3$ is a hydrogen atom, alkyl group, amino group substituted alkylcarbonylamino; $R^4$ is a hydrogen atom, alkyl group, carboxy group a group of formula (2):

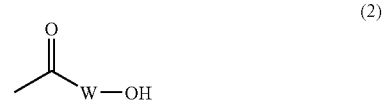

(2)

wherein W is an amino acid residue; m is 1 or 2; and n is an integer of 0 to 2, with the proviso that when n is 0, $R^3$ is a hydrogen atom or an alkyl group, or a pharmaceutically acceptable salt thereof, and its use in cancer immunotherapy.

11 Claims, 5 Drawing Sheets

OTHER PUBLICATIONS

Yoshihiro Oka, et al., Cancer Immunotherapy Targeting Wilms' Tumor Gene WT1 Product, The American Association of Immunologists, vol. 164, 2000, pp. 1873-1880.

Akihiro Tsuboi, "Cytotoxic T-Lymphocyte Responses Elicited to Wilms' Tumor Gene WT1 Product by DNA Vaccination" Journal of Clinical Immunology, vol. 20, No. 3, 2000, pp. 195-202.

Masanori Makita, Antilung Cancer Effect of WT1-specific Cytotoxic T Lymphocytes, Clinical Cancer Research, vol. 8, Aug. 2002, pp. 2626-2631.

Yoshihiro Oka, et al., "Induction of WT1 (Wilms' tumor gene)-specific cytotoxic T lymphocytes by WT1 peptide vaccine and the resultant cancer regression", The National Academy of Sciences of the USA, vol. 101, No. 38, Sep. 21, 2004, pp. 13885-13890.

Gábor Mezõ, et al., "New Conjugation Strategies for Attachment of Cys Containing Epitope Peptides to Branched Chain Polypeptides", Proceedings of the European Peptides Symposium 25th Budapest, Aug. 30-Sep. 4, 1998 (1999), pp. 470-471.

* cited by examiner

Fig. 1
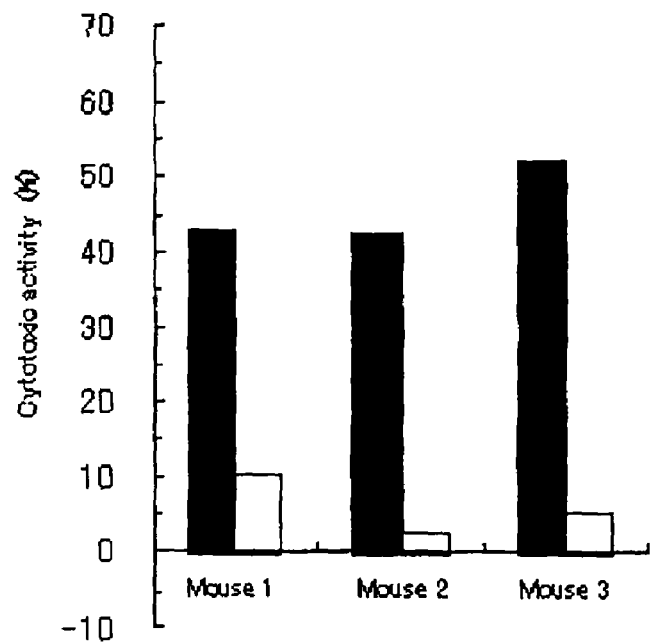
Fig. 2
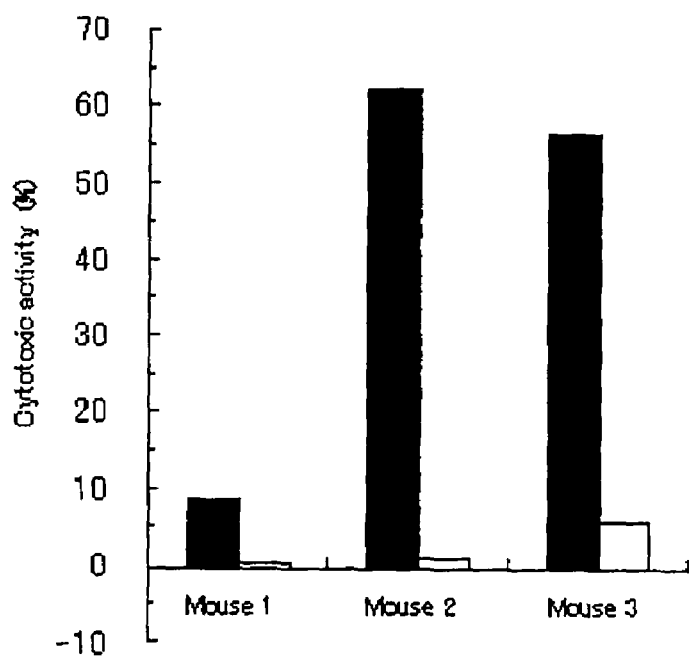
Fig. 3

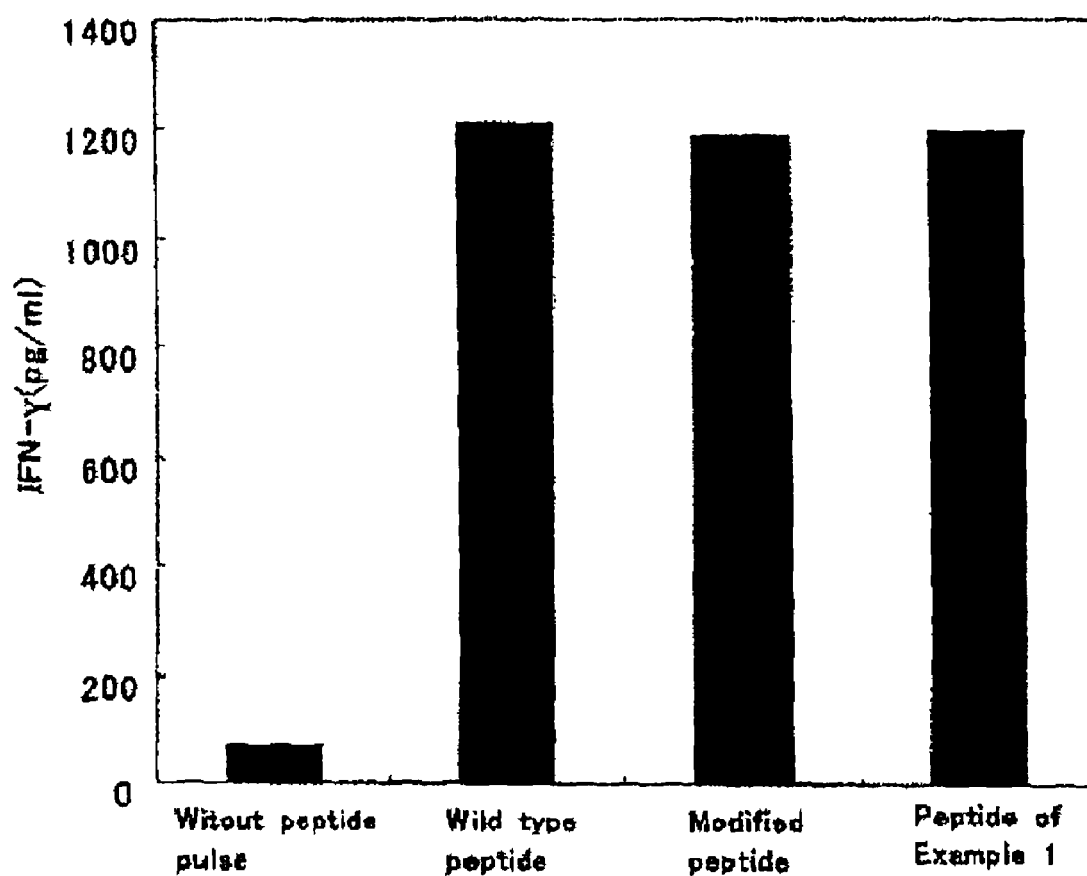

US 7,939,627 B2

PEPTIDES COMPRISING AN EPITOPE OF THE WILMS TUMOR GENE PRODUCT

TECHNICAL FIELD

The present invention relates to cancer vaccine therapy, especially to a novel peptide compound useful as a medicament for cancer immunotherapy. In particular, the present invention relates to a derivative of a cancer antigen peptide derived from WT1, which has CTL induction activity in vivo and is useful as cancer vaccine.

BACKGROUND ART

The cell mediated immunity, particularly a cytotoxic T cell (hereinafter, referred to as "CTL") plays a significant role in the in vivo rejection of cancer cells or virus-infected cells. CTLs recognize a complex between an antigen peptide ("cancer antigen peptide") derived from a cancer antigen protein and an MHC (major histocompatibility complex) class I antigen, which is referred to as "HLA antigen" in the case of human, on a cancer cell, and attack and kill the cell.

A cancer antigen peptide which binds to MHC class I molecule is generally known to be a peptide having 8-12 amino acid residues produced by intracellular processing of the protein. Thus, in general, a peptide having 8-12 amino acid residues derived from a cancer antigen protein can be a candidate for a cancer antigen peptide. When a glutamine residue or a cysteine residue is present in the cancer antigen peptide, those amino acid residues are spontaneously oxidized in air atmosphere in general. It is reported that such spontaneous oxidization decreases binding affinity of the peptide for MHC class I molecule and cognitive response to the peptide by T cell receptor (see nonpatent literatures 1 and 2).

The tumor suppressor gene WT1 of Wilms tumor (WT1 gene) has been isolated from chromosome 11p13 as one of the causative genes of Wilms tumor based on analysis of the WAGR syndrome that occurs as a complication of Wilms tumor, aniridia, urogenital abnormalities, mental retardation and so forth, and the amino acid sequence of WT1 is publicly known (see nonpatent literature 3). The WT1 gene is expressed with high frequency in human leukemia, and when leukemia cells are treated with WT1 antisense oligomers, the growth of the cells is inhibited. Thus, WT1 gene is thought to act to promote the growth of leukemia cells. Moreover, WT1 gene is also highly expressed in solid cancers such as gastric cancer, colon cancer, lung cancer, breast cancer, embryonal cancer, skin cancer, bladder cancer, prostate cancer, uterine cancer, cervical cancer and ovarian cancer, and the WT1 gene has been demonstrated to be a novel cancer antigen protein in leukemia and solid cancers (see nonpatent literatures 4 and 5). In addition, a cancer antigen peptide having a partial sequence of WT1 protein that is a wild type cancer antigen peptide was identified (see patent literatures 1 and 2).

Particularly, $WT1_{235-243}$ (Cys-Met-Thr-Trp-Asn-Gln-Met-Asn-Leu; SEQ ID NO: 1), that is a peptide spanning in positions 235 to 243 of the cancer antigen protein WT1, is a cancer antigen peptide having an activity to induce CTLs in HLA-A24-restricted manner (see nonpatent literature 6 and patent literature 1). The modified peptide (Cys-Tyr-Thr-Trp-Asn-Gln-Met-Asn-Leu; SEQ ID NO: 2, hereinafter it may be referred to as $WT1_{235-243}$ (2M→Y)), in which the methionine residue at position 2 of $WT1_{235-243}$ is replaced with tyrosine residue, has a higher binding affinity for the HLA-A24 antigen than the wild type peptide (see patent literature 3). The development of both wild type peptide $WT1_{235-243}$ and the modified peptide $WT1_{235-243}$ (2M→Y) as an immunotherapeutic agent is promising.

In addition, it is known that each of said wild type peptide and said modified peptide has a cysteine residue at the N-terminal site, oxidization of which in air atmosphere produces the dimer bound via disulfide bond, and said dimer may also work as a cancer antigen peptide (see patent literature 4).

Patent literature 1: WO 00/06602
Patent literature 2: WO 00/18795
Patent literature 3: WO 02/079253
Patent literature 4: WO 2004/063217
Nonpatent literature 1: Immunity., 6:273, 1997
Nonpatent literature 2: J. Immunol., 160:2099, 1998
Nonpatent literature 3: Cell, 60:509, 1990
Nonpatent literature 4: J. Immunol., 164:1873-80, 2000
Nonpatent literature 5: J. Clin. Immunol., 20, 195-202, 2000
Nonpatent literature 6: Clin. Cancer. Res. 8: 2626, 2002

DISCLOSURE OF INVENTION

A Problem to be Solved by the Invention

A problem to be solved by the present invention is to provide a novel peptide compound which has CTL induction activity in vivo and is useful as cancer vaccine in cancer immunotherapy.

A Means for Solving the Problem

The inventors earnestly conducted various studies on modification of the cancer antigen peptides $WT1_{235-243}$ and $WT1_{235-243}$ (2M→Y) derived from WT1 protein in order to produce a cancer antigen peptide having improved physical-chemical property, stability and bioactivity. In particular, they prepared the compounds modified from these peptides and examined the immunogenicity using HLA-A2402/Kb transgenic mice (see WO 02/47474, hereinafter they may be also referred to as HLA-A24 mice).

Consequently, they succeeded in preparing a peptide compound having improved physical-chemical property and stability by means of modifying cysteine residue (Cys) at the N-terminal site of $WT1_{235-243}$ or $WT1_{235-243}$ (2M→Y), especially modifying the thiol group of the cysteine residue at the N-terminal site. The peptide compound of the present invention has an improved immunogenicity and CTL induction activity. The T cells specifically induced by the present peptide compound are useful as a medicament for cancer immunotherapy due to their cross-reaction with wild type peptide $WT1_{235-243}$ which is originally presented by cancer cells.

So far, the peptide compound in which the cysteine residue of $WT1_{235-243}$ or $WT1_{235-243}$ (2M→Y) as the WT1 antigen peptide is modified was not known to show the immunogenicity enough to work as a cancer antigen. The present inventors firstly found that a peptide derivative prepared by condensing the thiol group of cysteine residue at the N-terminal with the thiol group of cysteine, glutathione or thioglycolic acid to form a disulfide bond, can be used as an effective cancer antigen.

The present invention was completed based on the finding as described above.

The present invention relates to
[1] a compound of the formula (1):

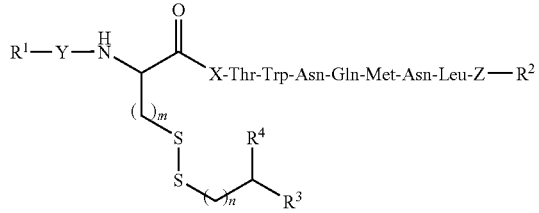

(1)

wherein X is a tyrosine residue or a methionine residue; each of Y and Z is independently selected from a single bond and a divalent peptide group consisting of 1-10 amino acid residues,
$R^1$ is hydrogen or alkyl,
$R^2$ is hydroxyl, amino, alkylamino or dialkylamino,
$R^3$ is hydrogen, alkyl, amino, alkylamino, dialkylamino or substituted or unsubstituted alkylcarbonylamino,
$R^4$ is hydrogen, alkyl, carboxy, carbamoyl, alkylcarbamoyl, dialkylcarbamoyl or a group of the formula (2):

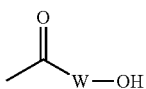

(2)

wherein W is an amino acid residue,
m is 1 or 2, and
n is an integer of 0-2, with the proviso that when n is 0, $R^3$ is hydrogen or alkyl,
or a pharmaceutically acceptable salt thereof;
[2] the compound according to above [1], or a pharmaceutically acceptable salt thereof,
wherein said substituted alkylcarbonylamino represented by $R^3$ is alkylcarbonylamino substituted by one or two substituent group selected from the group consisting of carboxy, amino, alkylamino and dialkylamino;
[3] the compound according to above [1] or [2], or a pharmaceutically acceptable salt thereof,
$R^3$ is hydrogen or a group of the formula (3):

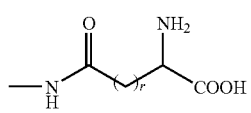

(3)

wherein r is an integer of 1-3, and
$R^4$ is carboxy or a group of the formula (2'):

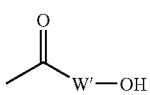

(2')

wherein W' is a glycine residue or β-alanine residue;

[4] the compound according to above [3], or a pharmaceutically acceptable salt thereof,
wherein $R^3$ is a group of the formula (3'):

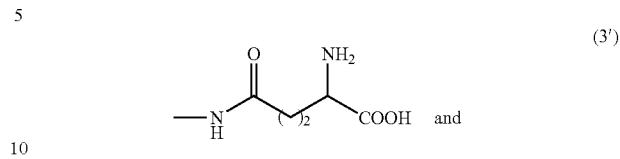

(3')

and $R^4$ is carboxymethylcarbamoyl;
[5] the compound according to above [3], or a pharmaceutically acceptable salt thereof,
wherein $R^3$ is hydrogen and $R^4$ is carboxy;
[6] the compound of the formula (1'):

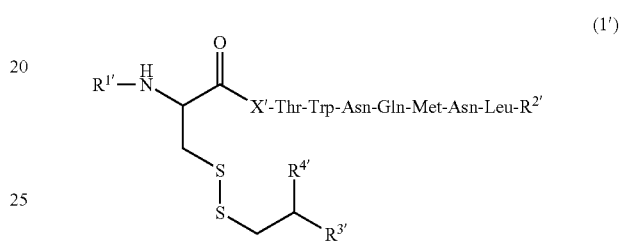

(1')

wherein X' is a tyrosine residue or a methionine residue,
$R^{1'}$ is hydrogen or alkyl,
$R^{2'}$ is hydroxyl, amino, alkylamino or dialkylamino,
$R^{3'}$ is amino, alkylamino, dialkylamino or substituted or unsubstituted alkylcarbonylamino, and
$R^{4'}$ is carboxy, carbamoyl, alkylcarbamoyl or dialkylcarbamoyl,
or a pharmaceutically acceptable salt thereof;
[7] an antibody which specifically binds to the compound according to any one of above [1]-[6] or a pharmaceutically acceptable salt thereof;
[8] an antigen-presenting cell which presents a complex of the compound according to any one of above [1]-[6] or a pharmaceutically acceptable salt thereof and HLA-A24 antigen;
[9] a CTL induced by the compound according to any one of above [1]-[6] or a pharmaceutically acceptable salt thereof;
[10] the CTL according to above [9], which recognizes a complex of the compound according to any one of above [1]-[6] or a pharmaceutically acceptable salt thereof and HLA-A24 antigen;
[11] the CTL according to above [9], which recognizes a complex of the peptide of SEQ ID No:1 and HLA-A24 antigen;
[12] a pharmaceutical composition comprising the compound according to any one of above [1]-[6] or a pharmaceutically acceptable salt thereof, the antigen-presenting cell according to above [8] or the CTL according to any one of above [9]-[11], together with a pharmaceutically acceptable carrier;
[13] the pharmaceutical composition according to above [12], which is used as a cancer vaccine;
[14] a use of the compound according to any one of above [1]-[6] or a pharmaceutically acceptable salt thereof, the antigen-presenting cell according to above [8] or the CTL according to any one of above [9]-[11] for preparing a cancer vaccine;
[15] a medicament for cancer immunotherapy comprising the compound according to any one of above [1]-[6] or a pharmaceutically acceptable salt thereof, the antigen-presenting cell according to above [8] or the CTL according to any one of above [9]-[11] as an active ingredient; or

[16] a method for the treatment or prevention of cancer, which comprises administrating a therapeutically or prophylactically effective amount of the compound according to any one of above [1]-[6] or a pharmaceutically acceptable salt thereof, the antigen-presenting cell according to above [8] or the CTL according to any one of above [9]-[11] to a patient who is positive for HLA-A24 and positive for WT1 in need of the treatment or prevention of the cancer.

The Effect Produced by the Present Invention

A novel peptide compound useful as a medicament for cancer immunotherapy, for example, a cancer antigen derived from WT1 which has CTL induction activity in vivo and is useful as cancer vaccine is provided by the present invention. The peptide of the present invention, which is prepared by modification of mercapto group of cysteine residue located at N-terminal of $WT1_{235-243}$ or $WT1_{235-243}$ (2M→Y) with maintaining the activity as a cancer antigen peptide, has improved physical-chemical property and stability and thus, it can be widely used for treatment or research. In particular, the novel peptide of the present invention has advantages such as convenience in handling without taking care of decrease in activity due to in vitro treatment, exhibition of stable therapeutic effect and so on.

BRIEF DESCRIPTION OF DRAWINGS

FIG. 1 is a graph showing cytotoxic activity (Specific Lysis) induced by the peptide compound of Example 1 using three mice individually (black bar in the figure). In the figure, white bar shows the results obtained using cells not pulsed with any peptide (The same is applicable to the following figures).

FIG. 2 is a graph showing cytotoxic activity (Specific Lysis) induced by the peptide compound of Example 2 using three mice individually.

FIG. 3 is a graph showing cytotoxic activity (Specific Lysis) induced by the peptide compound of Example 3 using three mice individually.

BEST MODE FOR CARRYING OUT THE INVENTION

Figure 4:
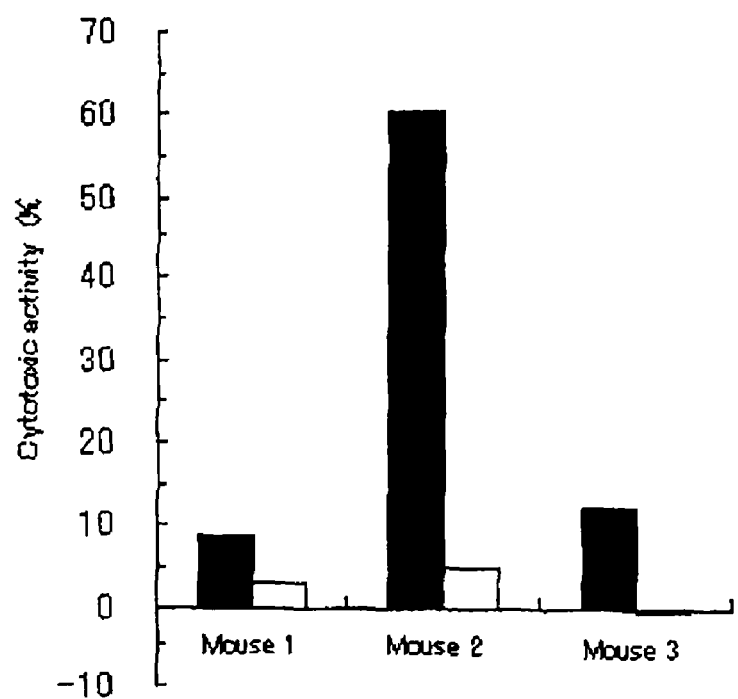
FIG. 4 is a graph showing cytotoxic activity (Specific Lysis) induced by the peptide compound of Example 4 using three mice individually.
Figure 5:
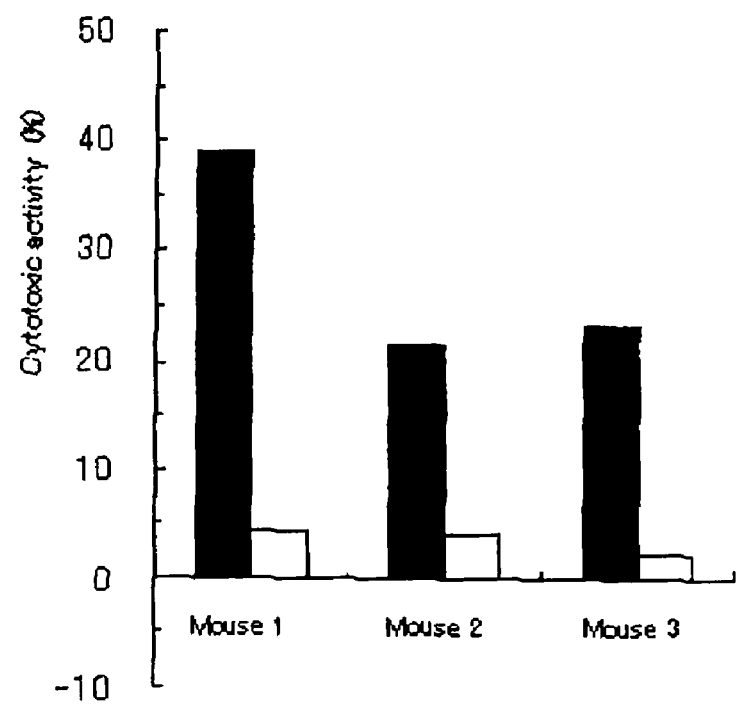
FIG. 5 is a graph showing cytotoxic activity (Specific Lysis) induced by the peptide compound of Example 5 using three mice individually.
Figure 6:
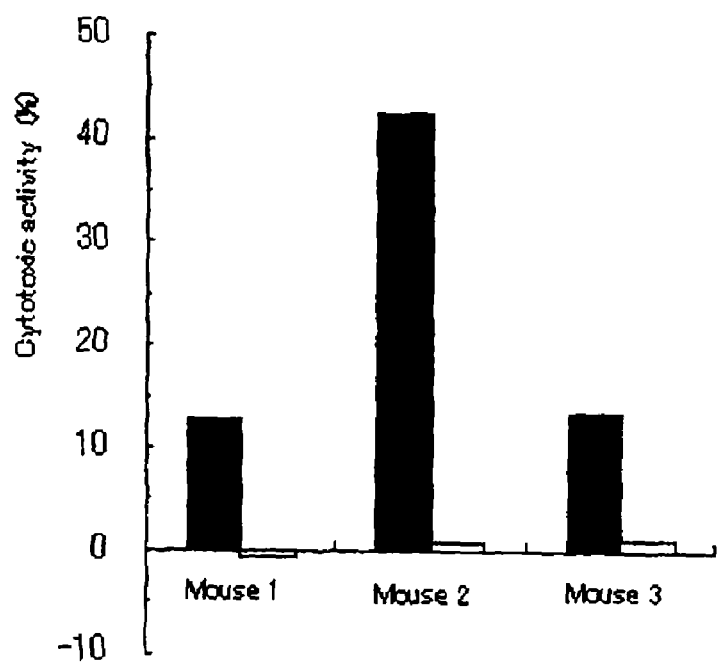
FIG. 6 is a graph showing cytotoxic activity (Specific Lysis) induced by the peptide compound of Example 6 using three mice individually.

As used in the specification and the drawings of the present application, the following abbreviations are used for each amino acid residue.
Ala: alanine residue
Arg: arginine residue
Asn: asparagine residue
Asp: aspartic acid residue
Cys: cysteine residue
Gln: glutamine residue
Glu: glutamic acid residue
Gly: glycine residue
His: histidine residue
Ile: isoleucine residue
Leu: leucine residue
Lys: lysine residue
Met: methionine residue
Phe: phenylalanine residue
Pro: proline residue
Ser: serine residue
Thr: threonine residue
Trp: tryptophan residue
Tyr: tyrosine residue
Val: valine residue As used in the specification, "amino acid residue" includes natural or nonnatural α-amino acid residue, β-amino acid residue, γ-amino acid residue and δ-amino acid residue. For example, "amino acid residue" includes a natural α-amino acid (for example, Ala, Arg, Asn, Asp, Cys, Gln, Glu, Gly, His, Ile, Leu, Lys, Met, Phe, Pro, Ser, Thr, Trp, Tyr or Val), ornithine residue, homoserine residue, homocysteine residue, β-alanine, γ-aminobutanoic acid or δ-aminopentanoic acid.

The above described amino acid can be either L-enantiomer or D-enantiomer when it is an optical isomer. L-enantiomer is more preferable.

In the specification, the amino acid sequence of the peptide compound is described according to the conventional style where the N-terminal amino acid residue is located on the left side and the C-terminal amino acid residue is located on the right side.

(1) Peptide Compound

In a first aspect, the present invention relates to the compound of the above described formula (1) or a pharmaceutically acceptable salt thereof.

In the formula (1), preferably, X represents a tyrosine residue (Tyr).

In the formula (1), "the divalent peptide groups consisting of 1-10 amino acid residues" represented by Y and Z include the same or different divalent peptide group consisting of 1-10 amino acid residues without any limitation of the amino acid sequence. For example, said divalent peptide group consisting of 1-10 amino acid includes an amino acid sequence comprised in the amino acid sequence of human WT1 (Cell, 60:509, 1990, GenBank Acc. No. A38080). For example, Y may represent a divalent peptide group consisting of ten amino acid residues of 225 to 234 of human WT1, which is described as follows: Asn-Leu-Tyr-Gln-Met-Thr-Ser-Gln-Leu-Glu (SEQ ID No: 3) or a divalent peptide group having a fragment of SEQ ID NO: 3, in which 1-9 amino acid residues at N-terminal are deleted. In addition, for example, Z may represent a divalent peptide group consisting of ten amino acid residues of 244 to 253 of human WT1, which is described as follows: Gly-Ala-Thr-Leu-Lys-Gly-Val-Ala-Ala-Gly (SEQ ID No: 4) or a divalent peptide group having a fragment of SEQ ID NO: 4, in which 1-9 amino acid residues at C-terminal are deleted. Preferably, each of Y and Z may represent a single bond.

In the specification, the alkyl group includes, for example, a linear or branched alkyl group having 1-6 carbon atoms. For example, the alkyl group includes methyl, ethyl, propyl, 1-methylethyl, butyl, 1-methylpropyl, 2-methylpropyl, 1,1-dimetylethyl, pentyl and the like.

In the specification, the alkylamino group includes, for example, a linear or branched alkylamino group having 1-6 carbon atoms. For example, the alkylamino group includes methylamino, ethylamino, propylamino, 1-methylethylamino, butylamino, 1-methylpropylamino, 2-methylpropylamino, 1,1-dimetylethylamino, pentylamino and the like.

In the specification, the dialkylamino group includes, for example, an amino group substituted by two same or different and linear or branched alkyl groups having 1-6 carbon atoms. For example, the dialkylamino group includes dimethylamino, ethylmethylamino, diethylamino, dipropylamino, methylpropylamino, butylmethylamino, methylpentylamino and the like.

In the specification, the "alkyl" of the alkylcarbonylamino group includes the alkyl group as described above. The "alkyl" of the alkylcarbamoyl group includes the same alkyl as that of alkylamino group as described above. The "alkyl" of the dialkylcarbamoyl group includes the same alkyl as that of dialkyiamino group as described above, wherein two "alkyl" may be same or different.

Each of R¹ and R² preferably represents a hydrogen atom.

When R³ represents a substituted alkylcarbonylamino group, the substituted group of alkylcarbonylamino group includes, for example, carboxy, hydroxyl, amino, alkylamino and dialkylamino, wherein said alkylcarbonylamino group may be substituted by same or different 1-4, preferably 1 or 2 substituted groups.

The amino acid residue represented by W in the formula (2) may include glycine residue (Gly), preferably.

The peptide compound of the present invention includes, for example, compounds of the following formulae (4)-(9):

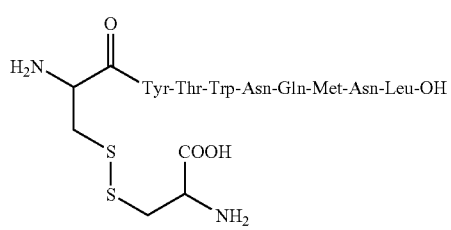

(4)

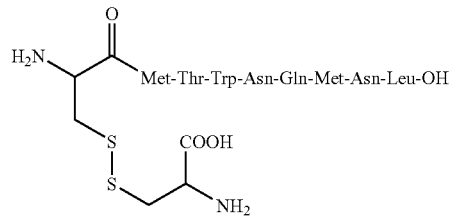

(5)

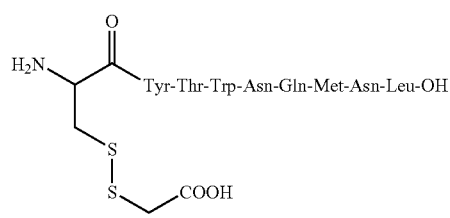

(6)

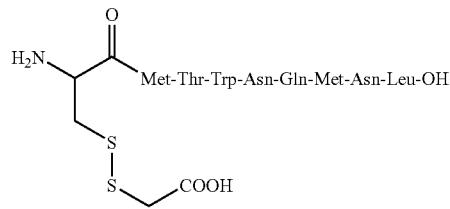

(7)

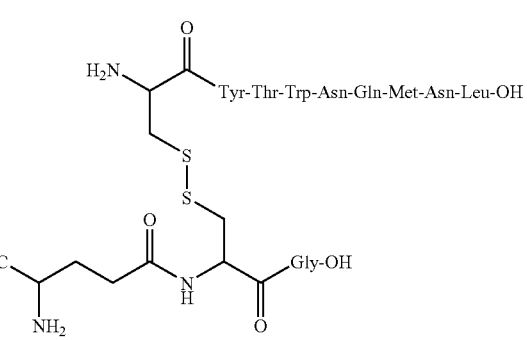

(8)

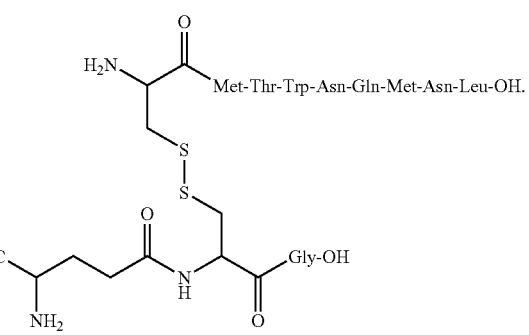

(9)

The peptide compounds of the present invention may be prepared according to the method described in the Examples of the specification or a method usually used in peptide synthesis. Examples of such preparations are those as described in the literatures including "Peptide Synthesis", Interscience, New York, 1966; "The Proteins", Vol. 2, Academic Press Inc., New York, 1976; "Pepuchido-Gosei", Maruzen Co. Ltd., 1975; "Pepuchido-Gosei-no-Kiso-to-Jikkenn", Maruzen Co. Ltd., 1985; and "Iyakuhin-no-Kaihatu, Zoku, vol. 14, Peputido-Gosei", Hirokawa Shoten, 1991. Example of the method for preparing the peptide of the present invention includes a method for preparing the peptide according to Fmoc method or Boc method by means of solid-phase synthesizer or a method for preparing the peptide by means of sequential condensation of Boc-amino acid or Z-amino acid according to the liquid-phase synthesis method, wherein Fmoc represents 9-fluorenylmethyloxycarbonyl group, Boc represents tert-butoxycarbonyl group and Z represents benzyloxycarbonyl group, respectively.

A functional group such as amino, carboxyl and mercapto group of the intermediate compound in the synthesis of the compound of the present invention may be protected by a suitable protective group, and the protected compound may be deprotected using a conventional technique of protection/deprotection, if required. A suitable protective group and a method for the protection and the deprotection are described for example, in Protective Groups in Organic Synthesis 2nd Edition (John Wiley & Sons, Inc.; 1990), in detail.

In particular, an example of the method for preparing the compound of the present invention is a method as described in the following reaction formulae:

[Reaction formula 1]

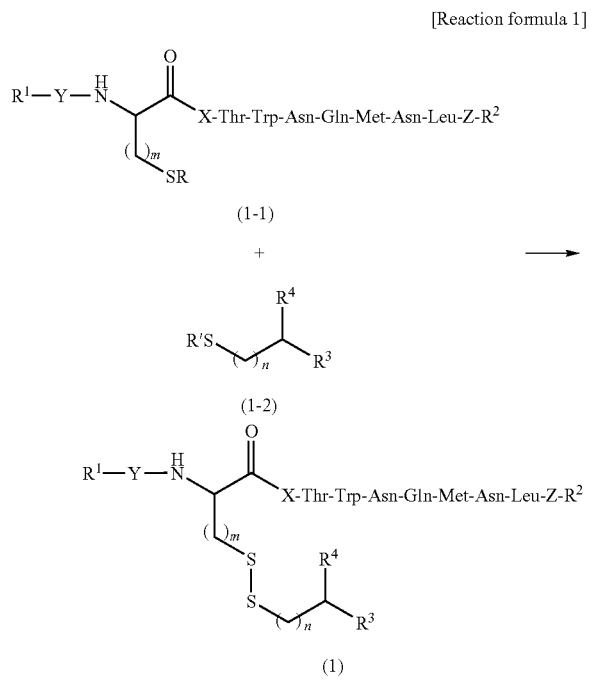

wherein X, Y, Z, $R^1$, $R^2$, $R^3$, $R^4$, m and n are same as described above, respectively. Each of R and R' independently represents a hydrogen atom or a protective group for mercapto group.

The example of said protective group for mercapto group includes, for example, acetoamidomethyl or trityl.

The compound of the formula (1) may be prepared by oxidizing the compound of the formula (1-1) and the compound of the formula (1-2) in an inert solvent.

The oxidization may be conducted by a conventional method normally applied in the peptide synthesis to form a disulfide bond. For example, a disulfide bond may be formed by mixing two intermediates having mercapto group in a suitable solvent and oxidizing them. A conventional method for oxidization such as air oxidation and iodine oxidation may be used. The solvent may be water, acetic acid, methanol, chloroform, DMF or DMSO or a mixture thereof. The oxidation reaction sometimes gives a mixture of the symmetrical and the asymmetrical disulfide compounds. The desired asymmetrical disulfide compound may be prepared by purification of the mixture such as purification using various kinds of chromatography, purification according to recrystallization method and the like.

Alternatively, an intermediate having an activated mercapto group is mixed with another intermediate having a mercapto group to produce a selective disulfide bonding. Examples of the intermediate having an activated mercapto group include, for example, a compound having a mercapto group bound to Npys group (3-nitro-2-pyridine sulfenyl group).

Alternatively, after one of the intermediates having a mercapto group is mixed with, for example, 2,2'-dithiobis(5-nitropyridine) to activate the mercapto group, the other intermediate is added to the resulting mixture to form a selective disulfide bonding (Tetrahedron Letters. Vol. 37. No. 9, pp. 1347-1350).

The compound of the formula (1-1) may be prepared according to a liquid-phase or a solid-phase peptide synthesis method which is well known by those skilled in the art.

In addition, in the case where the compound of the formula (1-1) is a N terminally-alkylated compound, N-alkyl amino acid or N,N-dialkyl amino acid which may be, if required, protected by a protective group may be used as a N-terminal amino acid. The N-alkyl amino acid or N, N-dialkyl amino acid may be commercially available or prepared according to a method well known by those skilled in the art, in which, for example, an amino acid or protected amino acid of starting material is reacted with an alkylhalide in the presence of base. For example, N-terminal amino group may be appropriately alkylated by reacting amino acid which is protected by t-butoxycarbonyl group with alkylhalide in the presence of base such as sodium hydride as illustrated in the following [Reaction formula 2].

[Reaction Formula 2]

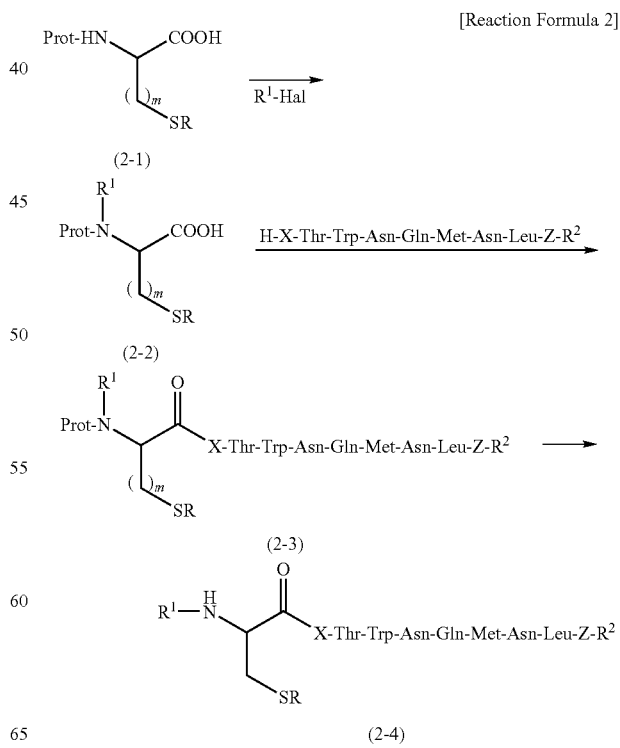

wherein each of X, Z, R¹, R², m and R is the same as described above, Hal represents a bromine atom or an iodine atom, and Prot represents a protective group.

Further, in the case where the compound is a C terminally-amidated or alkylamidated compound, an amidated or alkylamidated amino acid may be used as a C-terminal amino acid residue of the starting material.

The compound of the present invention or intermediates in the synthesis thereof may be purified according to the method well known by those skilled in the art. For example, the purification may be conducted by means of various kinds of chromatography (e.g. silica-gel column chromatography, ion-exchange column chromatography, gel filtration chromatography or reversed phase chromatography) or recrystallization. The solvent for the recrystallization may be, for example, alcohols such as methanol, ethanol and 2-propanol, ethers such as diethylether, esters such as ethyl acetate, aromatic hydrocarbons such as benzene and toluene, ketones such as acetone, hydrocarbons such as hexane, aprotic solvents such as dimethylformamide and acetonitrile, water or mixed solvents thereof. Other method used for the purification may be the method as described in volume 1 of Jikken-kagakukoza (edited by Chemical Society of Japan, Maruzen).

In the case where the compound of the present invention has one or more asymmetric centers, the material (amino acid) having the asymmetric center may be used for preparing it according to the conventional method. In addition, the optical resolution may be carried out in the appropriate step of the production process to improve the optical purity of the compound of the present invention. For example, the optical resolution may be carried out according to the diastereomer method in which the compound or the intermediate of the present invention is mixed with optically active acid (e.g. monocarboxylic acid such as mandelic acid, N-benzyloxy-alanine and lactic acid, dicarboxylic acid such as tartaric acid, o-diisopropylidene tartaric acid and malic acid or sulfonic acid such as camphorsulfonic acid and bromocamphorsulfonic acid) in an inactive solvent (e.g. alcohols solvent such as methanol, ethanol and 2-propanol, ethers such as diethylether, esters solvent such as ethyl acetate, hydrocarbons solvent such as toluene, aprotic solvents such as acetonitrile or mixed solvents thereof) to prepare the salt form. In the case where the compound or the intermediate of the present invention has an acid functional group such as carboxy group, the optical resolution may be carried out by forming the salt with optically active amine (e.g. organic amine such as α-phenethylamine, quinine, quinidine, cinchonidine, cinchonine and strychnine).

The reaction for forming the salt may be conducted at a temperature ranging from a room temperature to boiling point of the solvent. For the sake of improving the optical purity, it is preferable that the temperature is once increased up to about the boiling point of the solvent. The yield may be improved, if required by cooling the mixture, when the precipitated salt is recovered by filtration.

The optically active acid or amine is appropriately used in the amount of about 0.5 to about 2.0 equivalents to the substrate, preferably in the amount of about 1 equivalent to the substrate. If required, the crystal may be recrystallized in an inactive solvent (e.g. alcohols such as methanol, ethanol and 2-propanol, ethers such as diethylether, esters such as ethyl acetate, hydrocarbons such as toluene, aprotic solvents such as acetonitrile or mixed solvents thereof) to obtain the highly purified optically active salt. In addition, if required, the optically resolved salt may be treated with acid or base according to the conventional method in order to obtain the compound of free form.

A pharmaceutically acceptable salt includes an acid addition salt and a base addition salt. For example, the acid addition salt includes a salt with an inorganic acid such as hydrochloride, hydrobromide, sulfate, hydroiodide, nitrate and phosphate, and a salt with an organic acid such as citrate, oxalate, acetate, formate, propionate, benzoate, trifluoroacetate, maleate, tartrate, methanesulfonate, benzenesulfonate and paratoluenesulfonate. The base addition salt includes a salt with an inorganic base such as sodium salt, potassium salt, calcium salt, magnesium salt and ammonium salt, a salt with an organic base such as triethylammonium salt, triethanol ammonium salt, pyridinium salt and diisopropylammonium salt, and further a salt of amino acid such as basic or acidic amino acid including arginine, asparagine acid and glutamic acid.

In addition, the present invention comprises the solvate of the peptide compound represented by the formula (1) or a pharmaceutically acceptable salt thereof including hydrate or ethanol solvate. Further, the present invention comprises any possible stereoisomers including any diastereomers and enantiomers of the compound represented by formula (1), and any crystal forms thereof.

In the course of preparing a peptide compound including the steps of condensing an optically active α-amino acid, removing various kinds of protecting group or releasing the peptide from resin, by-products including a peptide with amino acid deletion, a peptide degraded by hydrolysis, oxidization or the like, and a peptide having a epimerized amino acid are usually produced. At laboratory scale, a combination of various chromatographies (e.g. silica-gel column chromatography, ion-exchange column chromatography, gel filtration or reversed phase chromatography) may be used for removing those impurities so as to obtain a highly purified peptide compound. However, it is not easy to obtain the highly purified peptide compound at industrial scale for the sake of providing it as a medicine.

The peptide compound of the present invention has a physical-chemical property which enables the large scale production of the bulk pharmaceuticals. In particular, the peptide compound of the present invention has a property including high solubility, high stability in the solution or a tendency not to turn into a gel when it is condensed so that the highly purified peptide compound may be easily prepared as a bulk pharmaceutical even in the large scale by means of the purification using column chromatography such as reversed phase chromatography.

The peptide compound of the present invention is useful for an active ingredient comprised in CTL inducer or cancer vaccine for cancer immunotherapy. The peptide compound of the present invention has a high immunogenicity and high CTL induction activity as shown in Examples of the present specification. The CTL induced by the peptide compound of the present invention can surprisingly recognize a wild type peptide of WT1 originally carried by cancer cells. Thus, the peptide compound of the present invention is useful for a medicament for the treatment or prevention (including prevention of a recurrence) of cancer expressing WT1 gene such as gastric cancer, colon cancer, lung cancer, breast cancer, embryonal cancer, skin cancer, bladder cancer, prostate cancer, uterine cancer, cervical cancer, and ovarian cancer.

(2) Antibodies of the Present Invention

In a second aspect, the present invention relates to antibodies which specifically bind to a peptide represented by the formula (1) or pharmaceutically acceptable salt thereof (hereinafter they may be referred to as "antibodies of the invention). The antibodies of the invention are not limited to a specific antibody, and may be a polyclonal antibody or a monoclonal antibody prepared using a peptide of the present invention as an immunogen.

The antibodies of the present invention are not limited to a specific antibody as long as they specifically bind to the peptide compounds of the invention, and specific examples include an antibody that specifically binds to a peptide represented by any one of the formulae (4)-(9) as described above.

A method for preparing the antibodies have been already well known, and the antibodies of the present invention may be prepared according to conventional methods (Current protocols in Molecular Biology edit. Ausubel et al. (1987) Publish. John Wiley and Sons. Section 11.12 to 11.13, Antibodies; A Laboratory Manual, Lane, H, D. et al. ed., Cold Spring Harber Laboratory Press Publisher, New York 1989).

Specifically, the antibodies may be prepared using the peptide compounds of the present invention (for example, a compound represented by any one of the formulae (4)-(9)) as an immunogen to immunize a non-human animal such as a rabbit, followed by obtaining the antibodies from the serum of the immunized animal in a conventional manner. On the other hand, monoclonal antibodies may be prepared by immunizing a non-human animal such as a mouse with the compound of the present invention, for example, a compound represented by any one of the formulae (4)-(9), and preparing hybridoma from the splenocytes obtained from the animal and myeloma cells by means of cell fusion, followed by obtaining the antibodies from the hybridoma (Current protocols in Molecular Biology edit. Ausubel et al. (1987) Publish. John Wiley and Sons. Section 11.4 to 11.11).

The antibodies directed to the peptide compounds of the invention may be prepared in a manner that the immunological reaction is enhanced using diverse adjuvants suitable for the host. Examples of the adjuvants include Freund's adjuvant, mineral gels such as aluminium hydroxide, surfactants such as lysolecithin, Pluronic polyol, polyanions, peptides, oil emulsions, Keyhole limpet Hemocyanin, and dinitrophenol, and human adjuvants such as BCG (*Bacille Calmette Guerin*) and *Corynebacterium-parvum*.

As described above, the antibodies that recognize the compound of the present invention, as well as the antibodies that neutralize the activity of the compound may be readily prepared by immunizing appropriately an animal with the compounds of the present invention in a conventional manner. Such antibodies may be used in affinity chromatography, immunological diagnosis, and the like. Immunological diagnosis may be appropriately selected from immunoblotting, radioimmunoassay (RIA), enzyme-linked immunosorbent assay (ELISA), a fluorescent or luminescent assay, and the like. The immunological diagnosis is useful to diagnose cancers expressing the WT1 gene, such as gastric cancer, colon cancer, lung cancer, breast cancer, embryonal cancer, skin cancer, bladder cancer, prostate cancer, uterine cancer, cervical cancer, and ovarian cancer.

(3) Antigen-Presenting Cells of the Present Invention

In a third aspect, the present invention relates to antigen-presenting cells on which a complex between a compound of the present invention and an HLA-A24 antigen is presented.

Examples described hereinafter demonstrate that the administration of the compounds of the present invention induces CTLs. That is, antigen-presenting cells on which a complex between the compound of the present invention and an HLA-A24 antigen is presented, are generated in the peripheral blood mononuclear cells, and then CTLs which specifically recognize the cells presenting such a complex are induced. Those antigen-presenting cells on which a complex between an HLA-A24 antigen and the compound of the present invention is presented, are useful in cell therapy (DC therapy) as described hereinafter.

Antigen-presenting cells of the present invention are not limited to a specific cell as long as they presents on their surfaces a complex between the compound of the present invention and an HLA-A24 antigen. They specifically include, for example, antigen-presenting cells of dendritic cells on which a complex between the compound represented by any one of the formulae (4)-(9) and an HLA-A24 antigen is presented.

Antigen-presenting cells used in cell therapy (DC therapy) may be prepared by isolating cells having an antigen-presenting ability from a cancer patient and pulsing the resulting cells ex vivo with the compound of the present invention so that the cells present a complex between a compound of the present invention and an HLA-A24 antigen on their cell surface. In this context, the "cell having an antigen-presenting ability" is not limited to a specific cell as long as it is a cell expressing on the surface an HLA-A24 antigen that has an ability to present the compound of the present invention, and dendritic cells, which is believed to have an especially high antigen-presenting ability, are preferably exemplified.

Antigen-presenting cells of the present invention may be prepared, for example, by isolating cells having an antigen-presenting ability from a cancer patient, pulsing the cells ex vivo with the compound of the invention (e.g. the compound of any one of the formulae (4)-(9)), and preparing a complex between an HLA-A24 antigen and the compound of the present invention (Cancer Immunol. Immunother., 46: 82,1998, J. Immunol., 158: p 1796, 1997, Cancer Res., 59: p 1184, 1999). When dendritic cells are used, antigen-presenting cells of the present invention may be prepared, for example, by isolating lymphocytes from peripheral bloods of a cancer patient using Ficoll method, removing the non-adherent cells, incubating the adherent cells in the presence of GM-CSF and IL-4 to induce dendritic cells, and incubating and pulsing the resultant dendritic cells with the compound of the present invention.

The antigen-presenting cells thus prepared as described above are useful as an active ingredient comprised in a CTL inducer or a cancer vaccine for cell therapy (DC therapy) as described hereinafter.

(4) CTLs of the Present Invention

The peptide compounds of the present invention are derived from human WT1 and have a CTL induction activity (immunogenicity) in HLA-A24-restricted manner. In a fourth aspect, the present invention relates to CTL induced by a peptide compound of the present invention.

Examples described hereinafter demonstrate that the administration of the peptide compounds of the present invention induces CTLs. That is, antigen-presenting cells, on which a complex between a compound of the present invention and an HLA-A24 antigen is presented, are generated in the peripheral blood mononuclear cells, and then CTLs which specifically recognize the cells presenting such a complex are induced. Those CTLs induced by the peptide compound of the present invention are useful in adoptive immunotherapy as described hereinafter.

CTLs of the present invention are not limited to a specific CTL as long as they are induced by the peptide compound of the present invention, and particularly include CTLs recognizing a complex between the compound represented by any one of the formulae (4)-(9) and an HLA-A24 antigen and CTLs recognizing a complex between the wild type peptide (WT1$_{235-243}$: SEQ ID No:1) and an HLA-A24 antigen.

CTLs used in adoptive immunotherapy may be prepared by, for example, isolating peripheral lymphocytes from a patient and stimulating the resulting peripheral lymphocytes in vitro with the compound of the present invention (e.g. the compound represented by any one of the formulae (4)-(9)) (Journal of Experimental Medicine 1999, 190: 1669).

The CTLs of the present invention prepared as described above are useful as an active ingredient comprised in a cancer vaccine for an adoptive immunotherapy.

Pharmaceutical Compositions Usable as Cancer Vaccines

Compounds of the present invention, antigen-presenting cells of the present invention and CTLs of the present invention as described above (1)-(4) may be used as an active ingredient comprised in CTL inducer, that is to say a cancer vaccine, when formulated into a form as appropriate for those respective substances, which are illustrated below.

1) Cancer Vaccines Comprising a Compound of the Present Invention or a Pharmaceutical Salt thereof as an Active Ingredient The compound of the present invention has CTL induction activity. CTLs induced by the compound of the present invention can destroy cancers via their cytotoxic activity and the lymphokine productions. Thus, the compounds of the present invention can be used as an active ingredient comprised in a cancer vaccine for treatment or prevention of cancers. In the embodiment, the invention provides a cancer vaccine which comprises as an effective ingredient the compounds of the invention (a pharmaceutical composition usable as cancer vaccines). When the cancer vaccine of the invention is administered to a cancer patient positive for HLA-A24 and positive for WT1, the compound (e.g. the compound represented by any one of the formulae (4)-(9)) is presented on an HLA-A24 antigen of antigen-presenting cells, and then CTLs specific for the presented complex comprising the HLA-A24 antigen efficiently proliferate, and destroy cancer cells. In this way, treatment or prevention of cancers is achieved. The cancer vaccines of the invention can be used to treat or prevent cancers which involve the elevated expression level of the WT1 gene, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer. In this connection, as another embodiment, the invention provides a method for the treatment or prevention of cancer, which comprises administering an effective amount of the cancer vaccine of the present invention to a cancer patient who is positive for an HLA-A24, and positive for WT1.

The cancer vaccine comprising a compound of the present invention as an active ingredient may comprise either a single cancer antigen peptide, that is to say, CTL epitope (e.g. a compound represented by any one of the formulae (4)-(9)) as an active ingredient, or an epitope peptide connected to another cancer antigen peptide (a CTL epitope) or a helper epitope as an active ingredient. Recently, it has been demonstrated that an epitope peptide connected to a plurality of CTL epitopes (antigen peptides) has an activity to induce CTLs effectively in vivo. For example, Journal of Immunology 1998, 161: 3186-3194 describes that an about 30-mer epitope peptide to which HLA-A2, -A3, -A11, B53-restricted CTL epitopes (antigen peptides) derived from the cancer antigen protein PSA are linearly-connected induced CTLs specific for the relevant CTL epitope in vivo. Also, it has been demonstrated that an epitope peptide in which a CTL epitope and a helper epitope are linearly-connected effectively induced CTLs. When a peptide of the invention in the form of such epitope peptides is administered, the peptide is introduced into antigen-presenting cells, and then subjected to intracellular degradation to generate respective antigen peptides, which bind an HLA antigen to form complexes. The complexes are presented compactly on the cell surface of the antigen-presenting cells, and then CTLs specific for the complexes efficiently proliferate in vivo, and destroy cancer cells. In this way, the treatment or prevention of cancers is achieved.

Cancer vaccines comprising the peptide of the present invention as an active ingredient may be also administered together with a pharmaceutically acceptable carrier such as a suitable adjuvant, or in a particulate dosage form in order to effectively establish the cellular immunity. For such purpose, those adjuvants described in the literature (Clin. Microbiol. Rev., 7:277-289, 1994) are applicable, and specifically include bacterium-derived components, GM-CSF, cytokines such as Interleukin-2, Interleukin-7, Interleukin-12 and the like, plant-derived components, marine organism-derived component, mineral gels such as aluminium hydroxide, surfactants such as lysolecithin and Pluronic polyol, polyanions, peptides, and oil emulsions (emulsion formulations). The bacterium-derived components include lipid A, monophosphoryl lipid A which is a derivative of lipid A, killed bacterium (e.g. Mycobacterium such as BCG), protein or polynucleotide derived from bacterium, Freund's Incomplete Adjuvant, Freund's Complete Adjuvant, cell wall component (e.g. BCG-CWS), trehalose-dimycolate (TDM) and the like. Also, liposomal formulations, particulate formulations in which the ingredient is bound to beads having a diameter of several μm, or formulations in which the ingredient is attached to lipids are also possible.

Administration may be achieved by, for example, intradermal, subcutaneous, intramuscular or intravenous injection. Although the dose of the compound of the present invention in the formulations may vary depending on the disease to be treated, the age and the weight of the patient, and the like, it is typical to administer 0.0001 mg to 1000 mg, preferably 0.001 mg to 1000 mg, more preferably 0.1 mg to 10 mg of a compound of the invention every several days to every several months.

2) Cancer Vaccines Comprising the Antigen-Presenting Cell of the Present Invention as an Active Ingredient The present invention provides a cancer vaccine which comprises the antigen-presenting cell of the present invention as an active ingredient.

Recently, cell therapy (DC therapy) has been reported wherein lymphocytes are isolated from the peripheral bloods of a cancer patient, and the dendritic cells induced from the lymphocytes are pulsed in vitro with an antigen peptide or the like to prepare antigen-presenting cells, which are then returned into the patient via a subcutaneous injection or the like (Cancer Immunol. Immunother., 46: 82, 1998, J. Immunol., 158: p 1796, 1997, Cancer Res., 59: p 1184, 1999, Cancer Res., 56: p 5672, 1996, J. Immunol., 161: p 5607, 1998, J. Exp. Med., 184: p 465, 1996). Thus, the antigen-presenting cell of the present invention can be used as an active ingredient in a cancer vaccine in cell therapy.

The cancer vaccine which comprises the antigen-presenting cells of the invention as an active ingredient preferably contains physiological saline, phosphate buffered saline (PBS), medium, or the like to stably maintain the antigen-presenting cells. It may be administered, for example, intravenously, subcutaneously, or intradermally. The dose is exemplified by those described in the aforementioned literatures.

By reintroducing the cancer vaccine into the body of the patient, specific CTLs are efficiently induced in patients positive for HLA-A24, and positive for WT1 so as to achieve the treatment or the prevention of the cancers. The cancer vaccine which comprises the antigen-presenting cells of the invention as an active ingredient can be used to treat or prevent cancers wherein the level of the WT1 gene expression is elevated, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

3) Cancer Vaccines Comprising the CTL of the Present Invention as an Active Ingredient The present invention provides a cancer vaccine which comprises as an active ingredient the CTL of the invention (a pharmaceutical composition usable as cancer vaccines). The CTL of the present invention are useful in adoptive immunotherapy as described hereinafter.

For melanomas, it has been observed that an adoptive immunotherapy achieves a therapeutic effect, wherein tumor-infiltrating T cells isolated from the patient himself/herself are cultured ex vivo in large quantities, and then returned into the patient (J. Natl. Cancer. Inst., 86:1159, 1994). Likewise, in mouse melanoma, suppression of metastasis has been observed by in vitro stimulation of splenocytes with cancer antigen peptide TRP-2, thereby proliferating CTLs specific for the cancer antigen peptide, and administering said CTLs into a melanoma-grafted mouse (J. Exp. Med., 185:453, 1997). This resulted from in vitro proliferation of CTLs that specifically recognize the complex between an HLA antigen and the cancer antigen peptide on antigen-presenting cells. Accordingly, a method for treating cancers, which comprises stimulating in vitro peripheral blood lymphocytes from a patient using the compound of the present invention to proliferate tumor-specific CTLs in vitro, and subsequently returning the CTLs into the patient, is believed to be useful. Thus, the CTLs of the invention may be used as an active ingredient comprised in cancer vaccine used in adoptive immunotherapy.

A cancer vaccine which comprises the CTLs of the present invention as an active ingredient preferably contains physiological saline, phosphate buffered saline (PBS), medium, or the like to stably maintain the CTLs. It may be administered, for example, intravenously, subcutaneously, or intradermally. The dose is exemplified by those described in the aforementioned literatures.

By reintroducing the cancer vaccine into the body of the patient, cytotoxic effect of CTLs on cancer cells is enhanced in the patient positive for HLA-A24 and positive for WT1, and destroys cancer cells, so as to achieve the treatment of the cancers. The cancer vaccine which comprises the CTL of the present invention as an active ingredient can be used to treat or prevent cancers which involve the elevated level of the WT1 gene expression. Examples of cancers include blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

The present invention is further illustrated by the following examples, but is not limited by those examples in any respect.

In the following examples, the compound of Example 2, the compound of Example 4 and the compound of Example 6 are derivatives of $WT1_{235-243}$ (SEQ ID No:1), and correspond to the derivative of $WT1_{235-243}$ modified with cystine, glutathione or thioglycolic acid, respectively. In addition, the compound of Example 1, the compound of Example 3 and the compound of Example 5 are derivatives of $WT1_{235-243}$ (2M→Y) (SEQ ID No:2), and correspond to the derivative of $WT1_{235-243}$ (2M→Y) modified with cystine, glutathione or thioglycolic acid, respectively.

EXAMPLE

The abbreviations used in the Examples are as follows:
Boc: t-butoxycarbonyl
Npys: 3-nitro-2-pyridine sulfenyl
t-Bu; t-butyl
Trt: triphenylmethyl
Fmoc: 9-fluorenylmethyloxycarbonyl
DMF: dimethylformamide
HOBT: N-hydroxybenzotriazole
DIPCI: diisopropylcarbodiimide Example 1

Synthesis of a Peptide of the Formula (4):

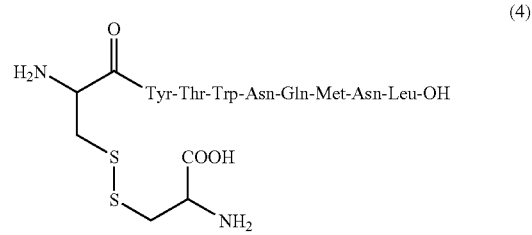

(4)

A peptide (1.5 g) prepared in Preparation 1 as described below and Boc-Cys(Npys)-OH (600 mg) were mixed in dimethylsulfoxide (20 ml) and the mixture was stirred at room temperature for 20 minutes. Acetonitrile (600 ml) was added to the reaction mixture, and the mixture was stirred on ice, and the resulting precipitate was collected by filtration. The solid on the filter was washed with acetonitrile and diethyl ether followed by drying under reduced pressure to prepare the peptide (1.65 g) in which Boc-Cys-OH was bounded by disulfide bonding. The resulting peptide (0.53 g) was dissolved in trifluoroacetic acid (5 ml) and the solution was stirred at room temperature for 10 minutes. After trifluoroacetic acid was evaporated under reduced pressure, the residue was dissolved in a mixed solution of acetonitrile-acetic acid-water (10/10/90) (110 ml) followed by purification using HPLC.
Pump: LC-8A type (SHIMADZU CORPORATION)
Column: YMC ODS-A 3 cmΦ×25 cmL, 10 μm
Eluent 1: $H_2O$/0.1% TFA
Eluent 2: $CH_3CN$/0.1% TFA
Flow rate: 20 ml/min
Detection: UV220 nm The crude peptide solution was charged onto the column equilibrated with 5% of Eluent 2. Then, 5% of Eluent 2 was run for 10 minutes and 15% of Eluent 2 was run for 15 minutes and thereafter, the concentration of Eluent 2 was increased by 0.1%/min. Fractions comprising the desired product were collected and acetonitrile was evaporated under reduced pressure followed by lyophilization to prepare the desired peptide (300 mg).

Mass spectrometry: LC-ESI/MS m/z=1292 [M+1]$^+$ (theoretical value=1291.5)

Example 2

Synthesis of a Peptide of the Formula (5):

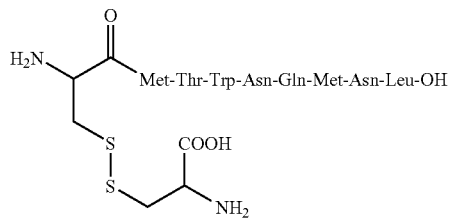

(5)

The desired peptide (104 mg) was prepared by reaction of a peptide (500 mg) prepared in Preparation 2 as described below with Boc-Cys(Npys)-OH (200 mg) followed by removal of Boc group in trifluoroacetic acid and purification by means of HPLC in the similar way to Example 1.

Mass spectrometry: LC-ESI/MS m/z=1260 [M+1]$^+$ (theoretical value=1259.5)

Example 3

Synthesis of a Peptide of the Formula (8):

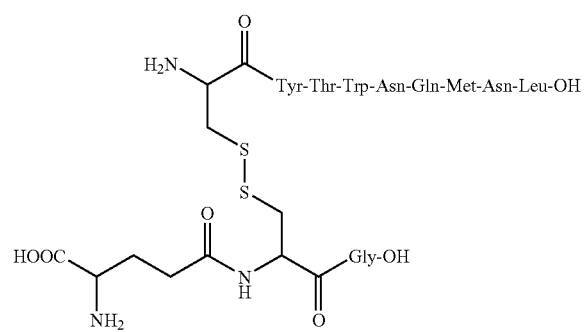

(8)

A peptide (240 mg) prepared in Preparation 1 and 2,2'-dithiobis(5-nitropyridine) (60 mg) were mixed in dimethylsulfoxide (6 ml) and the mixture was stirred at room temperature for 1 hour. Reduced glutathione (120 mg) was added to the reaction mixture followed by stirring at 30° C. for 1 hour. After reduced glutathione (60 mg) and dimethylsulfoxide (4 ml) were further added to the reaction mixture followed by stirring for 30 minutes, acetonitrile (200 ml) was added to the reaction mixture and then, the resulting precipitate was collected by filtration and dried under reduced pressure to prepare a crude peptide (440 mg). The resulting crude peptide was dissolved in the mixture (110 ml) of acetonitrile-acetic-acid and water (10/10/90) followed by purification using HPLC.

Pump: LC-8A type (SHIMADZU CORPORATION)
Column: YMC ODS-A 3 cmΦ×25 cmL, 10 μm
Eluent 1: H$_2$O/0.1% TFA
Eluent 2: CH$_3$CN/0.1% TFA
Flow rate: 20 ml/min
Detection: UV220 nm The crude peptide solution was charged onto the column equilibrated with 10% of Eluent 2. Then, 10% of Eluent 2 was run for 10 minutes and 17% of Eluent 2 was run for 15 minutes and thereafter, the concentration of Eluent 2 was increased by 0.05%/min. Fractions comprising the desired product were collected and acetonitrile was evaporated under reduced pressure followed by lyophilization to prepare the desired peptide (107 mg).

Mass spectrometry: LC-ESI/MS m/z=1477 [M+1]$^+$ (theoretical value=1477.5)

Example 4

Synthesis of a Peptide of the Formula (9):

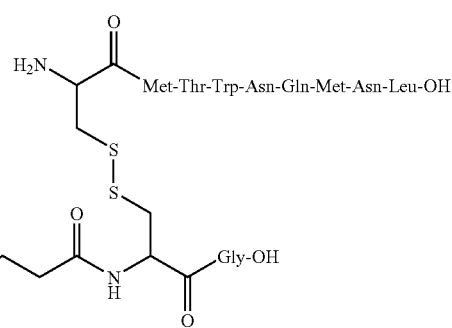

(9)

A peptide (120 mg) prepared in Preparation 2 and 2,2'-dithiobis(5-nitropyridine) (30 mg) were mixed in dimethylsulfoxide (3 ml) and the mixture was stirred at room temperature for 1 hour. Reduced glutathione (30 mg) was added to the reaction mixture followed by stirring at room temperature for 30 minutes and then, water (1 ml) and reduced glutathione (30 mg) were further added to the reaction mixture followed by stirring for 20 minutes. After acetonitrile (100 ml) was added to the reaction mixture, the resulting precipitate was collected by filtration and dried under reduced pressure to prepare a crude peptide (160 mg). The resulting crude peptide was dissolved in the mixture (55 ml) of acetonitrile-acetic acid-water (5/5/45) followed by purification using HPLC.
Pump: LC-6A type (SHIMADZU CORPORATION)
Column: YMC ODS-A 2 cmΦ×25 cmL, 10 μm
Eluent 1: H$_2$O/0.1% TFA
Eluent 2: CH$_3$CN/0.1% TFA
Flow rate: 10 ml/min
Detection: UV220 nm The crude peptide solution was charged onto the column equilibrated with 10% of Eluent 2. Then, 10% of Eluent 2 was run for 10 minutes and 17% of Eluent 2 was run for 15 minutes and thereafter, the concentration of Eluent 2 was increased by 0.05%/min. Fractions comprising the desired product were collected and acetonitrile was evaporated under reduced pressure followed by lyophilization to prepare the desired peptide (18 mg).

Mass spectrometry: LC-ESI/MS m/z=1445 [M+1]$^+$ (theoretical value=1445.5)

Example 5

Synthesis of a Peptide of the Formula (6):

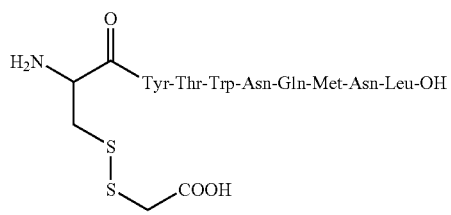

(6)

A peptide (240 mg) prepared in Preparation 1 and 2,2'-dithiobis(5-nitropyridine) (60 mg) were mixed in dimethylsulfoxide (6 ml) and the mixture was stirred at room temperature for 1 hour. Sodium thioglycolate (100 mg) was added to the reaction mixture followed by stirring at 30° C. for 30 minutes and then, sodium thioglycolate (50 mg), dimethylsulfoxide (4 ml) and water (2 ml) were further added to the reaction mixture followed by stirring for 30 minutes. After acetonitrile (200 ml) was added to the reaction mixture, the resulting precipitate was collected by filtration and dried under reduced pressure to prepare a crude peptide (305 mg). The resulting crude peptide was dissolved in the mixture (330 ml) of acetonitrile-acetic acid-water (30/30/270) followed by filtration and then, the resulting filtrate was purified using HPLC.
Pump: LC-8A type (SHIMADZU CORPORATION)
Column: YMC ODS-A 3 cmΦ×25 cmL, 10 μm
Eluent 1: H$_2$O/0.1% TFA
Eluent 2: CH$_3$CN/0.1% TFA
Flow rate: 20 ml/min
Detection: UV220 nm The crude peptide solution was charged onto the column equilibrated with 10% of Eluent 2. Then, 10% of Eluent 2 was run for 10 minutes and 20% of Eluent 2 was run for 15 minutes and 23% of Eluent 2 was run for 15 minutes and thereafter, the concentration of Eluent 2 was increased by 0.05%/min. Fractions comprising the desired product were collected and acetonitrile was evaporated under reduced pressure followed by lyophilization to prepare the desired peptide (15 mg).

Mass spectrometry: LC-ESI/MS m/z=1263 [M+1]$^+$ (theoretical value=1262.5)

Example 6

Synthesis of a Peptide of the Formula (7):

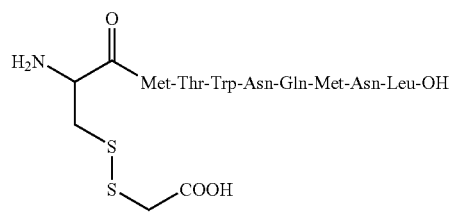

(7)

A peptide (240 mg) prepared in Preparation 2 and 2,2'-dithiobis(5-nitropyridine) (60 mg) were mixed in dimethylsulfoxide (6 ml) and the mixture was stirred at room temperature for 1 hour. Sodium thioglycolate (50 mg) was added to the reaction mixture followed by stirring at 30° C. for 30 minutes. In addition, after sodium thioglycolate (50 mg) was further added to the reaction followed by stirring at 30° C. for 1 hour, acetonitrile (200 ml) was added to the reaction mixture. The resulting precipitate was collected by filtration and dried under reduced pressure to prepare a crude peptide (194 mg). The resulting crude peptide was dissolved in the mixture (120 ml) of acetonitrile-acetic acid-water (10/20/90) followed by filtration and then, the resulting filtrate was purified using HPLC.
Pump: LC-8A type (SHIMADZU CORPORATION)
Column: YMC ODS-A 3 cmΦ×25 cmL, 10 μm
Eluent 1: H$_2$O/0.1% TFA
Eluent 2: CH$_3$CN/0.1% TFA
Flow rate: 20 ml/min
Detection: UV220 nm The crude peptide solution was charged onto the column equilibrated with 10% of Eluent 2. Then, 10% of Eluent 2 was run for 10 minutes and 18% of Eluent 2 was run for 15 minutes and thereafter, the concentration of Eluent 2 was increased by 0.1%/min. Fractions comprising the desired product were collected and acetonitrile was evaporated under reduced pressure followed by lyophilization to prepare the desired peptide (30 mg).

Mass spectrometry: LC-ESI/MS m/z=1230 [M+1]$^+$ (theoretical value=1230.4)

Example 7

Synthesis of a Peptide of the Formula (4):

1. Synthesis of Protected Peptide Resin (Boc-Cys(Boc-Cys-OH)-Tyr(tBu)-Thr(tBu)-Trp(Boc)-Asn(Trt)-Gln(Trt)-Met-Asn(Trt)-Leu-Alko-Resin)

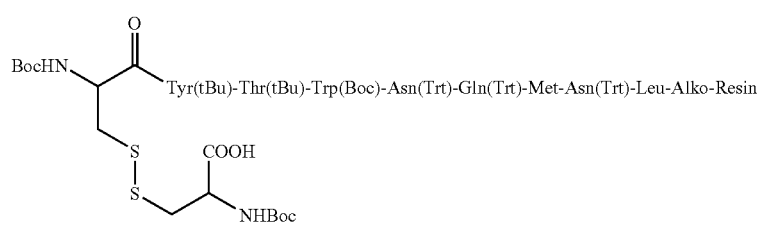

(10)

Fmoc-Leu-Alko-resin (wherein Alko is p-alkoxybenzyl alcohol) (10 g) (0.74 mmol/g, Watanabe Chemical Industries, Ltd.) was charged in a reaction vessel (500 ml, Type ACT90 solid phase synthesizer, Advanced ChemTech) and washed once with DMF or the like (Process 1). The resin was then treated with 25% piperidine (3 minutes×1, and 15 minutes×1) to cleave the Fmoc group (Process 2), and washed again with DMF or the like (Process 6) to remove piperidin. To the reaction vessel was added a solution of Fmoc-Asn(Trt)-OH (13.25 g) and HOBT (1-hydroxybenzotriazole) (3.4 g) in NMP (N-methylpyrrolidinone) (200 ml). After adding DIPCI (N,N'-diisopropylcarbodiimide) (3.42 ml), the mixture was stirred at room temperature for 60 minutes (Process 3). Then, the resin was washed with NMP (Process 4) and coupling reaction was conducted again using Fmoc-Asn(Trt)-OH (13.25 g), HOBT (3.4 g) and DIPCI (3.42 ml) (Process 3). After the resin was washed (Process 6), the resin was stirred in 25% $Ac_2O$ (acetic anhydride) for 3 minutes×1 and for 15 minutes×2 to cap the unreacted amino groups (Process 5). The resin was washed (Process 6) followed by deprotection (Process 2) and washing (Process 6) to prepare H-Asn(Trt)-Leu-Alko-resin. A coupling reaction was conducted using Fmoc-Met-OH (8.25 g), Fmoc-Gln(Trt)-OH (13.56 g), Fmoc-Asn(Trt)-OH (13.25 g), Fmoc-Trp(Boc)-OH (11.69 g), Fmoc-Thr(tBu)-OH (8.82 g), Fmoc-Tyr(tBu)-OH (10.2 g), and (Boc-Cys-OH)$_2$ (19.56 g) in a similar way, with the proviso that coupling was repeated three times in the case of difficulty in the coupling. After (Boc-Cys-OH)$_2$ (N,N'-t-butoxycarbonylcystine) located at N-terminal was condensed, washing (Process 6) was conducted followed by washing with diethylether (200 ml) twice and drying under reduced pressure to prepare Boc-Cys(Boc-Cys-OH)-Tyr(tBu)-Thr(tBu)-Trp(Boc)-Asn(Trt)-Gln(Trt)-Met-Asn(Trt)-Leu-Alko-Resin (the peptide-resin of the formula (10)) (22.87 g). The above processes for synthesis are summarized in the following Table.

TABLE 1

<Processes for Synthesis>

| Process | Reagent | Number of treatment | Time (min) |
|---|---|---|---|
| 1) Washing | DMF | 200 ml × 3 | 0.3 |
| | MeOH | 200 ml × 1 | 0.3 |
| | DMF | 200 ml × 3 | 0.3 |
| 2) Deprotection | 25% piperidine/ DMF | 200 ml | 3.0 |
| | | 200 ml | 15.0 |
| 3) Coupling | Amino-protected amino acid (3 eq. for each) 60 × 1 | | |
| | HOBT (3 eq.) DIPCI (3 eq.)/NMP 200 ml | | |
| 4) Washing | NMP | 200 ml × 2 | 0.3 |
| 5) Capping | 25% acetic anhydride/ DMF | 200 ml | 3.0 |
| | | 200 ml | 15.0 |
| 6) Washing | DMF | 200 ml × 5 | 0.3 |
| | MeOH | 200 ml × 1 | 0.3 |
| | DMF | 200 ml × 5 | 0.3 |

2. Deprotection of Protected Peptide Resin

The mixture (200 ml) of trifluoroacetic acid/ethanediol/$H_2O$/triisopropylsilane (94/2.5/2.5/1) was added to the protected peptide resin (Boc-Cys(Boc-Cys-OH)-Tyr(tBu)-Thr(tBu)-Trp(Boc)-Asn(Trt)-Gln(Trt) -Met-Asn(Trt)-Leu-Alko-Resin (22.87 g) obtained in accordance with the processes above, and the mixture was stirred at room temperature for 4 hours. After the reaction product was filtrated, the filtrate was added to diethylether (400 ml) with cooling on ice. The resulting precipitate was collected by filtration using glass filter and then, washed with diethylether and dried under reduced pressure to prepare the crude peptide (8.27 g).

3. Purification of Crude Peptide

The resulting crude peptide (2.76 g) was dissolved in the mixed solution of 20% acetic acid aqueous solution (1400 ml) and acetonitrile (35 ml) and the resulting insoluble substances were removed by filtration. The resulting crude peptide solution was purified using reversed-phase liquid chromatography.
Pump: LC-8A type (SHIMADZU CORPORATION)
Column: YMC ODS-A 5 cmΦ×50 cmL, 15-30 μm
Eluent 1: $H_2O$/0.1% TFA Eluent 2: $CH_3CN/0.1\%$ TFA
Flow rate: 60 ml/min
Detection: UV280 nm The crude peptide solution was charged onto the column equilibrated with 10% of Eluent 2. Then, 10% of Eluent 2 was run for 30 minutes and thereafter, the concentration of Eluent 2 was increased to 34% over 120 minutes. Fractions comprising the desired product were collected and acetonitrile was evaporated under reduced pressure followed by lyophilization to prepare the desired peptide: H-Cys(H-Cys-OH)-Tyr-Thr-Trp-Asn-Gln-Met-Asn-Leu-OH (the peptide of the formula (4)) (0.91 g).

Test Example 1

(Immunization of a Mouse (1))

An immunogenicity of each antigen peptide prepared by Examples 1-6 was evaluated using HLA-A2402/$K^b$ transgenic mice (see WO 02/47474 and hereinafter, the mice may be referred to as HLA-A24 mice). Three transgenic mice were used in the immunization of each peptide to evaluate the immunogenicity.

A pharmaceutical composition comprising each synthetic peptide was prepared as follows. Each of the synthetic peptides of Examples 1-3, 5, 6 was adjusted to 40 mg/ml in DMSO. Then, the solution (32.5 μl) was mixed with water for injection (540 μl). Further, the resulting solution (550 μl) was mixed with Freund's incomplete adjuvant (700 μl) (Montanide ISA51) using a glass syringe to prepare water-in-oil emulsion. The peptide of Example 4 was adjusted to 50 mg/ml in DMSO and synthetic helper paptide (FNNFTVSF-WLRVPKVSASHLE, SEQ ID No:5) was also adjusted to 20 mg/ml in DMSO. Then, 30 μl of both peptide solutions were mixed in water for injection (540 μl) followed by being mixed with the equal amount of Freund's incomplete adjuvant (IFA) to prepare water-in-oil emulsion.

The resulting preparation (200 μl) was injected into an HLA-A2402/$K^b$ transgenic mouse intradermally in the base of the tail for immunization. 7-8 days after initiation of the experiment, spleen was removed and grounded on the frosted part of glass slide, and splenocytes were collected and prepared. A portion of the splenocytes undergone hemolysis treatment with ACK buffer (0.15 M $NH_4Cl$, 10 mM $KHCO_3$, 0.1 mM EDTA, pH 7.2-7.4) was pulsed with the antigen peptide used in the immunization (100 μg/ml) for 1 hour and seeded into 24-well plate ($7 \times 10^6$ cells/well). Simultaneously, splenocytes not pulsed with any peptide ($7 \times 10^5$ cells/well) were added together, and stimulated in vitro and cultured at 37° C. for 5-6 days. The in vitro stimulation was carried out in RPMI-1640 medium supplemented with 10% FCS, 10 mM HEPES, 20 mM L-glutamine, 1 mM sodium pyruvate, 1 mM MEM nonessential amino acids, 1% MEM vitamin and 55 μM 2-mercaptoethanol.

5-6 days after initiation of restimulation, the test for cytotoxic activity was conducted according to the conventional manner. EL4-A2402/$K^b$ cells obtained by transforming EL-4 cells (DAINIPPON PHARMACEUTICAL CO., LTD., Catalogue No. 06-039) with an expression vector encoding HLA-A2402/$K^b$, and the EL4-A2402/$K^b$ cells pulsed with antigen peptide: $WT1_{235-243}$ or $WT1_{235-243}$ (2M→Y) were used as target cells (T). Specifically, cells pulsed with $WT1_{235-243}$ (2M→Y) were used for evaluation of peptides of Examples 1, 3 and 5, and cells pulsed with $WT1_{235-243}$ were used for evaluation of peptides of Examples 2, 4 and 6. These cells were labeled with $^{51}Cr$ (1.85 MBq/$10^6$ cells) and pulsed with the peptide at 100 μg/ml for an hour (The labeling was carried out for 2 hours, and 1 hour after the initiation of labeling, the peptide was added). $^{51}Cr$ release assay (J. Immunol., 159: 4753, 1997) was conducted to determine the cytotoxic activity of in vitro cultured splenocytes (E) to target cells (T). In this assay, E/T ratio was 80.

Figure 7:
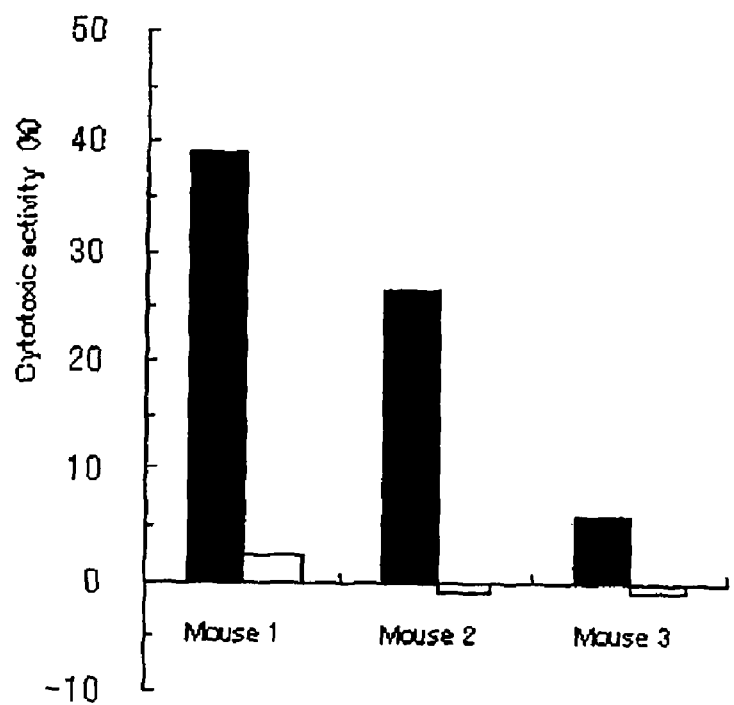
FIG. 7 is a graph showing dose-dependent cytotoxic activity (Specific Lysis) induced by the peptide compound of Example 1. The X axis shows dose per one individual mouse (600 µg, 200 µg, 60 µg and 20 µg), and Y axis shows cytotoxic activity (Specific Lysis). Each dose was administrated to three mice respectively and the results are shown as mean of the cytotoxic activities and the standard deviation (S.D.).

The results are shown in FIGS. 1-7. FIGS. 1-6 correspond to cytotoxic activities of peptide compounds of Examples 1-6 respectively. In the figures, the vertical axis shows cytotoxic activity (Specific Lysis), and the horizontal axis shows results of each of three mice individually. In addition, the results of dose dependence of the compound of Example 1 are shown in FIG. 7. In the figure, the vertical axis shows cytotoxic activity (Specific Lysis), and the horizontal axis shows individually administered dose (600 μg, 200 μg, 60 μg and 20 μg). In the figure, three mice were used per each dose, and mean and standard deviation (S.D.) of the cytotoxic activities are shown. As clearly understood from the figures, it was found that all of the synthetic peptides have CTL induction activity, that is to say, immunogenicity.

Test Example 2

(Immunization of a Mouse (2))

The peptide of Example 1 was adjusted to 40 mg/ml in DMSO. Then, the solution (32.5 μl) was mixed with water for injection (540 μl). Further, the resulting solution (550 μl) was mixed with Freund's incomplete adjuvant (700 μl) (Montanide ISA51 (registered trademark)) (SEPPIC, Inc, Paris, France) using a glass syringe to prepare water-in-oil emulsion.

The resulting preparation (200 μl) was injected into an HLA-A2402/$K^b$ transgenic mouse intradermally in the base of the tail for immunization. 7 days after initiation of the experiment, spleen was removed and splenocytes were prepared in a conventional manner (WO 02/47474). Then, tests were conducted using mouse IFN gamma ELISPOT set (Enzyme—Linked Immunospot) (Fujisawa, catalog No. BD-551083). The test was conducted according to the instructions attached to the set. $5 \times 10^5$ cells/well of splenocytes were plated and culture medium containing the peptide of Example 1, wild type peptide ($WT1_{235-243}$) or a peptide derived from influenza virus (ASNENMETM, negative control peptide which does not bind to HLA-A24) was added at the final concentration of $10^{-6}M$ followed by incubation using $CO_2$ incubator at 37° C. for 18 hours.

Figure 8:
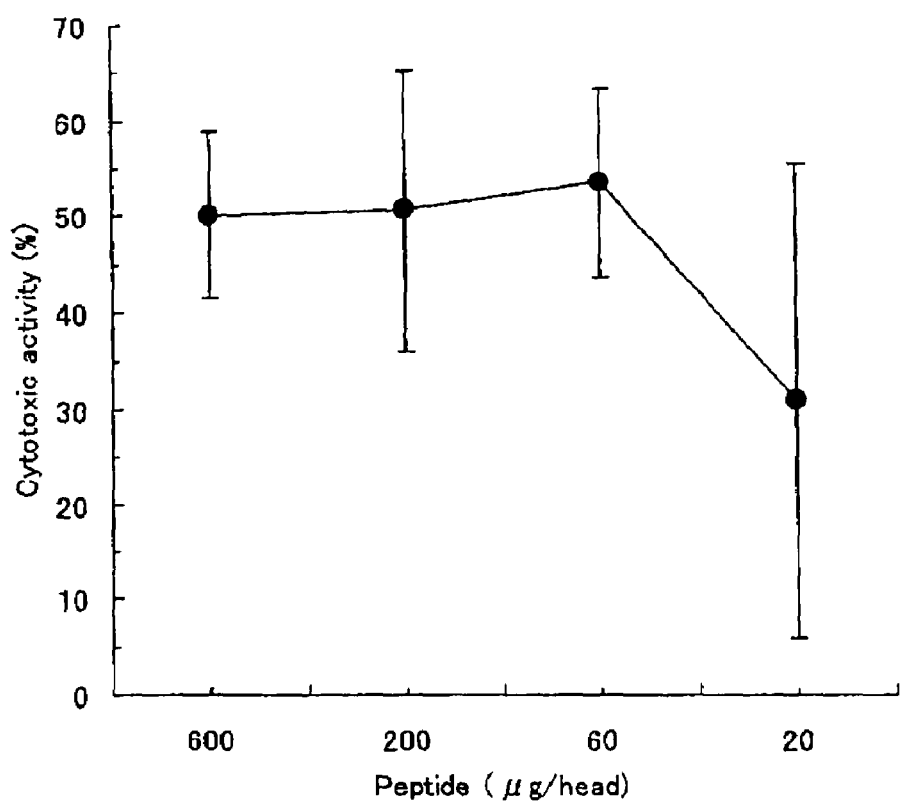
FIG. 8 is a graph showing reactivity of the peptide-specific T cell prepared by immunization of mice with the peptide compound of Example 1 to cells pulsed with various peptides. In the figure, the hatched bar shows the result obtained using cells pulsed with the wild type peptide ($WT1_{235-243}$), the black bar shows the result obtained using cells pulsed with the peptide compound of Example 1 and the white bar shows the result obtained using cells pulsed with a peptide derived from Influenza, respectively. In addition, in the figure, the vertical axis shows spots.

According to the attached instructions, the plate was washed and the number of spots was detected using KS Elispot Research System (Carl Zeiss). Elispot method is known as an alternative to a test for cytotoxic activity (J. Immunological Methods, 1995, 181, 45-54). The results are shown in FIG. 8. As a result, it was found that the peptide of Example 1 could induce HLA-A24 specific cell-mediated immunity which cross reacted with the wild type peptide.

Test Example 3

(Test Using Human PBMC)

Peripheral blood (50 ml) was taken using heparinized vacuum blood collection tube from HLA-A24 positive healthy subjects. The blood diluted two fold with PBS (−) was overlayered on Ficoll-Paque (Amersham Biosciences), the amount of which was half of the amount of the blood, followed by centrifugation for 20 minutes at 2000 rpm. A cell layer containing the peripheral blood mononuclear cells (PBMC) was collected and 3-4 times the amount of PBS (−)

was added thereto, followed by centrifugation for 10 minutes at 1800 rpm. The cell pellet was washed twice with PBS (−) and PMBC was collected.

The PMBC was suspended in medium for culturing lymphocyte (RPMI1640: AIM V=1:1, NEAA, 10% FCS) and cultured in a culture flask for two hours and nonadherent cells were collected. Using CD8+ T cell isolation kit II (Miltenyi Biotec), CD8 positive T cells were collected among the non-adherent cells. The adherent cells were cultured in the medium for culturing lymphocyte containing GM-CSF (1000 U/ml) and IL-4 (1000 U/ml) for 7 days. The floating cells were collected as an antigen-presenting cell fraction containing dendritic cells (DC). The collected cells were frozen for preservation until they are used for experiments.

The DC fraction prepared as above was pulsed with the peptide of Example 1 (50 μg/ml) by incubating the cells with the peptide in AIM-V medium containing mitomycin (50 μg/ml) for one hour. After washing with the medium three times, the peptide of Example 1 was further added (50 μg/ml) for one hour pulse to prepare antigen-presenting cells. On Day 0, antigen-presenting cells pulsed with the peptide were added to CD8 positive T cells to conduct the first stimulation, and the cell culture was started in medium for culturing lymphocyte containing IL-7 (10 ng/ml) using 24-well plate. On Day 7, T cells were collected and after washing them, peptide stimulation using antigen-presenting cells pulsed with the peptide was conducted in a similar way to the first stimulation. On the next day (Day 8), IL-2 was added so that the concentration was 50 U/ml. On Day 14, T cells were collected and the third stimulation was conducted in a similar way to the first or second stimulation. On the next day (Day 15), IL-2 was added so that the concentration was 50 U/ml. On Day 21, T cells were collected and frozen for preservation.

$1 \times 10^5$ cells of T cells of Day 21 were added to $2 \times 10^4$ cells of HLA-A2402 expressing VA13/A2402 cells pulsed with or without each of the peptides (wild type peptide ($WT1_{235-243}$), modified peptide ($WT1_{235-243}$(2M→Y) or the peptide of Example 1) and 18 hours later, the supernatant was collected to determine the amount of IFN-γ using ELISA.

Figure 9:
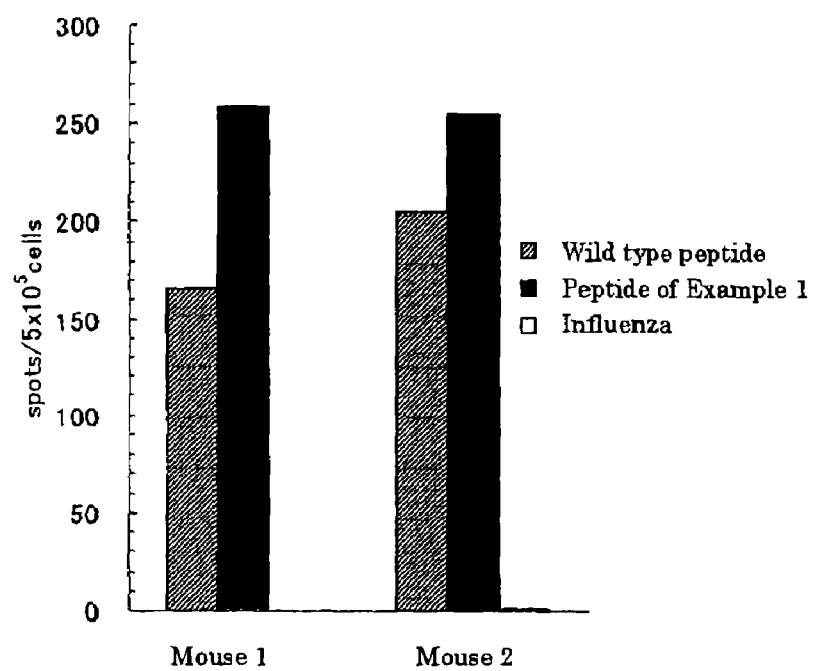
FIG. 9 is a graph showing reactivity of the peptide-specific T cell derived from human PBMC by stimulation with the peptide of Example 1 to cells pulsed with various peptides. In the figure, "wild type peptide" shows the result obtained using cells pulsed with the wild type peptide ($WT1_{235-243}$), the "modified peptide" shows the result obtained using cells pulsed with the modified peptide ($WT1_{235-243}$ (2M→Y)), the "peptide of Example 1" shows the results obtained using cells pulsed with the peptide compound of Example 1 and "without peptide pulse" shows the result obtained using cells not pulsed with any peptide, respectively. In addition, in the figure, the vertical axis shows the amount of produced interferon-γ.

The results of the peptide specific reactivity of T cells stimulated with the synthetic peptide of Example 1 were shown in FIG. 9. T cells stimulated with the synthetic peptide of Example 1 did not react with cells pulsed without the peptide, but they sufficiently reacted with cells pulsed with the peptide of Example 1. Thus, it was found that T cells specific for the peptide were induced. In addition, the induced T cells specific for the peptide reacted with the cells pulsed with the wild type peptide ($WT1_{235-243}$) as well as the cells pulsed with the modified peptide ($WT1_{235-243}$ (2M→Y)).

Preparation 1

1. Synthesis of Protected Peptide Resin (H-Cys(Trt)-Tyr(tBu)-Thr(tBu)-Trp (Boc)-Asn(Trt)-Gln(Trt)-Met-Asn(Trt)-Leu-Alko-Resin)

Fmoc-Leu-Alko-resin (wherein Alko is p-alkoxybenzyl alcohol) (10 g) (0.82 mmol/g, Watanabe Chemical Industries, Ltd.) was charged in a reaction vessel (500 ml, Type ACT90 solid phase synthesizer, Advanced ChemTech) and washed once with DMF or the like (Process 1). The resin was then treated with 25% Pip (piperidine) (3 minutes×1, and 15 minutes×1) to cleave the Fmoc group (Process 2), and washed again with DMF or the like (Process 1) to remove Pip. To the reaction vessel was added a solution of Fmoc-Asn(Trt)-OH (24.46 g) and HOBT (1-hydroxybenzotriazole) (6.28 g) in NMP (N-methylpyrrolidinone) (200 ml). After adding DIPCI (N,N'-diisopropylcarbodiimide) (6.3 ml), the mixture was stirred at room temperature for 30 minutes (Process 3). Thirty minutes later, the resin was washed with NMP (Process 4), and subjected to the coupling reaction once again using Fmoc-Asn(Trt)-OH (24.46 g), HOBT (6.28 g) and DIPCI (6.3 ml) (Process 5) to synthesize Fmoc-Asn(Trt)-Leu-Alko resin. The resultant resin was then converted to H-Asn(Trt)-Leu-Alko-resin by the deprotection of Process 2. After washing (Process 1), Fmoc-Met-OH 15.23 g, Fmoc-Gln(Trt)-OH 25.04 g, Fmoc-Asn(Trt)-OH 24.46 g, Fmoc-Trp(Boc)-OH 21.59 g, Fmoc-Thr(tBu)-OH 16.3 g, Fmoc-Tyr(tBu)-OH 18.84 g and Fmoc-Cys(Trt)-OH 24.01 g were added in series to conduct the coupling reaction (Process 3). In the coupling reaction using Fmoc-Thr(tBu)-OH, the reaction was repeated three times, and the resulting resin was washed with DMF and treated with 25% $A_{c_2}O$ (acetic anhydride) (15 minutes×2) for the capping of unreacted amino groups. After condensation of the N-terminal Fmoc-Cys(Trt)-OH, the deprotection (Process 2) and washing (Process 6) were conducted to obtain H-Cys(Trt)-Tyr(tBu)-Thr(tBu)-Trp(Boc)-Asn(Trt)-Gln(Trt)-Met-Asn(Trt)-Leu-Alko-Resin. The above processes for synthesis are summarized in the following Table.

TABLE 2

<Processes for Synthesis>

| Process | Reagent | Number of treatment | Time (min) |
|---|---|---|---|
| 1) Washing | DMF | 200 ml × 6 | 0.3 |
|  | MeOH | 200 ml × 1 | 0.3 |
|  | DMF | 200 ml × 3 | 0.3 |
| 2) Deprotection | 25% piperidine/ DMF | 200 ml | 3.0 |
|  |  | 200 ml | 15.0 |
| 3) Coupling |  | Amino-protected amino acid (5 eq. for each) 30 × 1 | |
|  |  | HOBT (5 eq.) DIPCI (5 eq.)/NMP 200 ml | |
| 4) Washing | NMP | 200 ml × 2 | 0.3 |
| 5) Coupling |  | Amino-protected amino acid (5 eq. for each) 30 × 1 | |
|  |  | HOBT (5 eq.) DIPCI (5 eq.)/NMP 200 ml | |
| 6) Washing | DMF | 200 ml × 5 | 0.3 |
|  | MeOH | 200 ml × 1 | 0.3 |
|  | DMF | 200 ml × 2 | 0.3 |

2. Deprotection of Protected Peptide Resin

The mixed solution of trifluoroacetic acid/ethanediol/$H_2O$/triisopropylsilane (94/2.5/2.5/1) (100 ml) was added to the protected peptide resin (H-Cys(Trt)-Tyr(tBu)-Thr(tBu)-Trp (Boc)-Asn(Trt)-Gln(Trt) -Met-Asn(Trt)-Leu-Alko-Resin) (10.0 g) as prepared above and the resulting mixture was stirred at room temperature for 4 hours. The reaction mixture was added to t-butylmethylether (625 ml) with cooling on ice and the resulting mixture was stirred for 15 minutes followed by filtration using a glass filter to obtain insoluble substances. After the residue on the filter was washed with t-butylmethylether (about 100 ml) five times, the residue on the filter was extracted with 6M guanidine hydrochloride aqueous solution (1 L) to prepare the crude peptide solution.

3. Purification of Crude Peptide

The resulting crude peptide solution was purified using reversed-phase liquid chromatography.
Pump: LC-8A type (SHIMADZU CORPORATION)
Column: YMC ODS-A 5 cmΦ×50 cmL, 15-30 μm
Eluent 1: $H_2O$/0.1% TFA
Eluent 2: $CH_3CN$/0.1% TFA
Flow rate: 60 ml/min
Detection: UV220 nm The crude peptide solution was charged onto the column which was equilibrated with 10% of Eluent 2 and kept in a water bath at 50° C. After 10% of Eluent 2 was run for 30 minutes, the concentration of Eluent 2 was increased to 20% over 40 minutes and further increased to 40% over 360 minutes. Fractions comprising a desired product were collected and acetonitrile was evaporated under reduced pressure followed by lyophilization to prepare the desired peptide: H-Cys-Tyr-Thr-Trp-Asn-Gln-Met-Asn-Leu-OH (SEQ ID No:2) (1.50 g).

amino acid analysis
Hydrolysis: 1% phenol/6N aqueous hydrochloric acid, 110° C., 10 hours
Analysis method: ninhydrin method
Asx: 1.96(2) Thr: 1.05(1) Glx: 1.06(1) Met: 1.05(1) *Leu: (1) Tyr: 0.87(1)
*) Leu=standard amino acid Theoretical value is described in ( ).
Mass analysis: LC-ESI/MS m/z=1173 [M+1]$^+$(theoretical value=1172.5)
Amino acid sequence analysis: The amino acid residues from Tyr at position 2 from the N-terminal to Leu at the C-terminal were sequentially confirmed.

Preparation 2

1. Synthesis of Protected Peptide Resin (H-Cys(Trt)-Met-Thr(tBu)-Trp(Boc)-Asn (Trt)-Gln(Trt)-Met-Asn (Trt)-Leu-Alko-Resin)

Fmoc-Leu-Alko-resin (wherein Alko is p-alkoxybenzyl alcohol) (10 g) (0.81 mmol/g, Watanabe Chemical Industries, Ltd.) was charged in a reaction vessel (500 ml, Type ACT90 solid phase synthesizer, Advanced ChemTech) and washed once with DMF or the like (Process 1). The resin was then treated with 25% Pip (piperidine) (3 minutes×1, and 15 minutes×1) to cleave the Fmoc group (Process 2), and washed again with DMF or the like (Process 1) to remove Pip. To the reaction vessel was added a solution of Fmoc-Asn(Trt)-OH (24.17 g) and HOBT (1-hydroxybenzotriazole) (6.2 g) in NMP (N-methylpyrrolidinone) (200 ml). After adding DIPCI (N,N'-diisopropylcarbodiimide) (6.2 ml), the mixture was stirred at room temperature for 30 minutes (Process 3). Thirty minutes later, the resin was washed with NMP (Process 4), and subjected to the coupling reaction once again using Fmoc-Asn(Trt)-OH (24.17 g), HOBT (6.2 g) and DIPCI (6.2 ml) (Process 5) to synthesize Fmoc-Asn(Trt)-Leu-Alko resin. The resultant resin was then converted to H-Asn(Trt)-Leu-Alko-resin by the deprotection of Process 2. After washing (Process 1), Fmoc-Met-OH 15.05 g, Fmoc-Gln(Trt)-OH 24.73 g, Fmoc-Asn(Trt)-OH 24.17 g, Fmoc-Trp(Boc)-OH 21.33 g, Fmoc-Thr(tBu)-OH 16.1 g, Fmoc-Met-OH 15.05 g and Fmoc-Cys(Trt)-OH 23.72 g were added in series to conduct the coupling reaction (Process 3). In the coupling reaction using Fmoc-Thr(tBu)-OH, the reaction was repeated three times, and the resulting resin was washed with DMF and treated with 25% $Ac_2O$ (acetic anhydride) (15 minutes×2) for the capping of unreacted amino groups. After condensation of the N-terminal Fmoc-Cys(Trt)-OH, the deprotection (Process 2) and washing (Process 6) were conducted to obtain H-Cys(Trt)-Met-Thr(tBu)-Trp(Boc)-Asn(Trt)-Gln(Trt)-Met-Asn(Trt)-Leu-Alko-Resin. The above processes for synthesis are the same as described in the table of Preparation 1.

2. Deprotection of Protected Peptide Resin

The mixture of trifluoroacetic acid/ethanediol/$H_2O$/triisopropylsilane (94/2.5/2.5/1) (130 ml) was added to the protected peptide resin (H-Cys(Trt)-Met-Thr(tBu)-Trp(Boc)-Asn(Trt)-Gln (Trt)-Met-Asn(Trt)-Leu-Alko-Resin) (13.0 g) as prepared above and the resulting mixture was stirred at room temperature for 4 hours. The reaction mixture was added to diethylether (800 ml) with cooling on ice and the resulting mixture was stirred for 15 minutes followed by filtration using a glass filter to obtain insoluble substances. After the residue on the filter was washed with diethylether (about 100 ml) five times, the residue on the filter was extracted with 6M guanidine hydrochloride aqueous solution (1.3 L) to prepare the crude peptide solution.

3. Purification of Crude Peptide

The resulting crude peptide solution was purified using reversed-phase liquid chromatography.
Pump: LC-8A type (SHIMADZU CORPORATION)
Column: YMC ODS-A 5 cmΦ×50 cmL, 15-30 μm
Eluent 1: $H_2O$/0.1% TFA
Eluent 2: $CH_3CN$/0.1% TFA
Flow rate: 60 ml/min
Detection: UV220 nm The crude peptide solution was charged onto the column which was equilibrated with 10% of Eluent 2 and kept in a water bath at 50° C. After 10% of Eluent 2 was run for 30 minutes, the concentration of Eluent 2 was increased to 20% over 40 minutes and further increased to 40% over 360 minutes. Fractions comprising a desired product were collected and acetonitrile was evaporated under reduced pressure followed by lyophilization to prepare the desired peptide: H-Cys-Met-Thr-Trp-Asn-Gln-Met-Asn-Leu-OH (SEQ ID No:1) (2.32 g).

amino acid analysis
Hydrolysis: 4N methanesulfonic acid, 110° C., 17 hours
Analysis method: ninhydrin method
Asx: 1.87(2) Thr: 0.93(1) Glx: 0.95(1) Met: 1.72(2) *Leu: (1) Trp: 0.80(1)
*) Leu=standard amino acid Theoretical value is described in ( )
Mass analysis: LC-ESI/MS m/z=1141 [M+1]$^+$ (theoretical value=1140.5)
Amino acid sequence analysis: The amino acid residues from Met at position 2 from the N-terminal to Leu at the C-terminal were sequentially confirmed.

INDUSTRIAL APPLICABILITY

The peptide compounds of the present invention are useful as an active ingredient comprised in a medicament for cancer immunotherapy.

Sequence Listing Free Text
SEQ ID No.1: peptide derivative
SEQ ID No.2: peptide derivative
SEQ ID No.3: peptide derivative
SEQ ID No.4: peptide derivative
SEQ ID No.5: helper synthetic peptide

The invention claimed is:

1. A compound of formula (1):

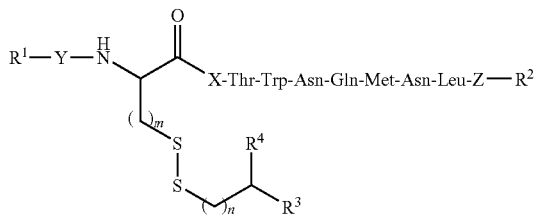

(1)

wherein X is a tyrosine residue or a methionine residue;
each of Y and Z is independently selected from the group consisting of a single bond and a divalent peptide group consisting of 1-10 amino acid residues, $R^1$ is hydrogen or alkyl, $R^2$ is hydroxyl, amino, alkylamino or dialkylamino, $R^3$ is hydrogen, alkyl, amino, alkylamino, dialkylamino or substituted or unsubstituted alkylcarbonylamino, $R^4$ is hydrogen, alkyl, carboxy, carbamoyl, alkylcarbamoyl, dialkylcarbamoyl or a group of formula (2):

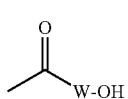

(2)

wherein W is an amino acid residue, m is 1 or 2, and n is an integer of 0-2, with the proviso that when n is 0, $R^3$ is hydrogen or alkyl, or a pharmaceutically acceptable salt thereof.

2. The compound of claim 1, or a pharmaceutically acceptable salt thereof,
wherein said substituted alkylcarbonylamino represented by $R^3$ is alkylcarbonylamino substituted by one or two substituent group selected from the group consisting of carboxy, amino, alkylamino and dialkylamino.

3. The compound of claim 1, or a pharmaceutically acceptable salt thereof,
wherein $R^3$ is hydrogen or a group of formula (3):

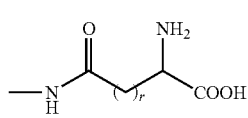

(3)

wherein r is an integer of 1-3, and $R^4$ is carboxy or a group of formula (2'):

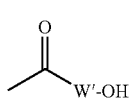

(2')

wherein W' is a glycine residue or β-alanine residue.

4. The compound of claim 3, or a pharmaceutically acceptable salt thereof,
wherein $R^3$ is a group of formula (3'):

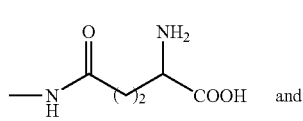

(3')

and $R^4$ is carboxymethylcarbamoyl.

5. The compound of claim 3, or a pharmaceutically acceptable salt thereof,
wherein $R^3$ is hydrogen and $R^4$ is carboxy.

6. A compound of formula (1'):

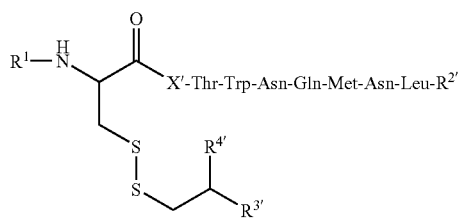

(1')

wherein X' is a tyrosine residue or a methionine residue, $R^{1'}$ is hydrogen or alkyl, $R^{2'}$ is hydroxyl, amino, alkylamino or dialkylamino, $R^{3'}$ is amino, alkylamino, dialkylamino or substituted or unsubstituted alkylcarbonylamino, and $R^{4'}$ is carboxy, carbamoyl, alkylcarbamoyl or dialkylcarbamoyl, or a pharmaceutically acceptable salt thereof.

7. An antigen-presenting cell on which a complex between the compound of claim 1 or a pharmaceutically acceptable salt thereof and HLA-A24 antigen is present.

8. The antigen presenting cell of claim 7, which is a dendritc cell.

9. A pharmaceutical composition comprising the compound of claim 1 or a pharmaceutically acceptable salt thereof in combination with a pharmaceutically acceptable carrier.

10. The compound of claim 1 which is of formula (4):

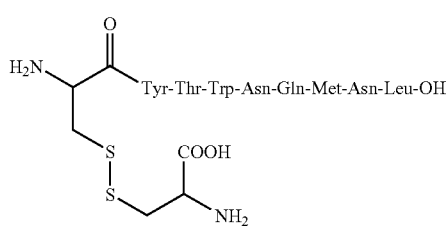

(4)

or a pharmaceutically acceptable salt thereof.

11. The compound of claim 1 which is of formula (5):

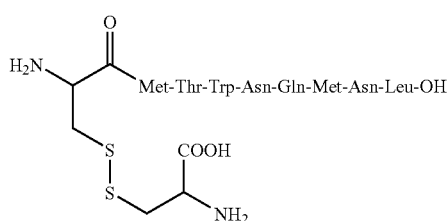

(5)

or a pharmaceutically acceptable salt thereof.

* * * * *

SEQUENCE LISTING

<160> NUMBER OF SEQ ID NOS: 5

<210> SEQ ID NO 1
<211> LENGTH: 9
<212> TYPE: PRT
<213> ORGANISM: Artificial sequence
<220> FEATURE:
<223> OTHER INFORMATION: Synthetic Peptide

<400> SEQUENCE: 1

Cys Met Thr Trp Asn Gln Met Asn Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Cys Tyr Thr Trp Asn Gln Met Asn Leu
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic Peptide

<400> SEQUENCE: 3

Asn Leu Tyr Gln Met Thr Ser Gln Leu Glu
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic Peptide

<400> SEQUENCE: 4

Gly Ala Thr Leu Lys Gly Val Ala Ala Gly
1               5                   10

<210> SEQ ID NO 5
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 5

Phe Asn Asn Phe Thr Val Ser Phe Trp Leu Arg Val Pro Lys Val Ser
1               5                   10                  15

Ala Ser His Leu Glu
            20